United States Patent
Hashimoto

(10) Patent No.: US 8,333,702 B2
(45) Date of Patent: Dec. 18, 2012

(54) ULTRASONIC PROBE AND ULTRASONIC DIAGNOSTIC APPARATUS

(75) Inventor: Shinichi Hashimoto, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1161 days.

(21) Appl. No.: 11/258,226

(22) Filed: Oct. 26, 2005

(65) Prior Publication Data

US 2006/0100513 A1  May 11, 2006

(30) Foreign Application Priority Data

Oct. 27, 2004 (JP) ............... P2004-312352
Dec. 2, 2004 (JP) ............... P2004-349372
Jan. 28, 2005 (JP) ............... P2005-020579

(51) Int. Cl.
*A61B 8/14* (2006.01)
(52) U.S. Cl. ............ 600/459; 600/437; 600/439; 601/2; 601/3
(58) Field of Classification Search .............. 600/459, 600/437, 439; 601/2, 3
See application file for complete search history.

(56) References Cited

U.S. PATENT DOCUMENTS

| | | | |
|---|---|---|---|
| 4,748,985 A | 6/1988 | Nagasaki | |
| 5,560,362 A | 10/1996 | Sliwa, Jr. et al. | |
| 5,721,463 A | 2/1998 | Snyder | |
| 5,961,465 A | 10/1999 | Kelly, Jr. et al. | |
| 2004/0059226 A1 | 3/2004 | Peszynski et al. | |
| 2004/0073118 A1 | 4/2004 | Peszynski et al. | |

FOREIGN PATENT DOCUMENTS

| | | |
|---|---|---|
| EP | 0 782 125 A2 | 7/1997 |
| JP | 9-140706 | 6/1997 |
| JP | 10-94540 | 4/1998 |
| JP | 2003-38485 | 2/2003 |
| JP | 2004-97402 | 4/2004 |
| WO | WO 03/090625 | 11/2003 |

*Primary Examiner* — Tse Chen
*Assistant Examiner* — Jason Ip
(74) *Attorney, Agent, or Firm* — Oblon, Spivak, McClelland, Maier & Neustadt, L.L.P.

(57) ABSTRACT

An ultrasonic probe comprises a transducer part, a heat-receiving part, a refrigeration unit and a cable unit. The cable unit includes a signal line, a refrigerant supply tube, a refrigerant ejection tube and a heat insulator. The heat-receiving part absorbs heat generated from the transducer part. The refrigerant supply tube supplies a refrigerant from the refrigeration unit to the heat-receiving part. The refrigerant ejection tube sends the refrigerant for ejecting heat of the heat-receiving part to the refrigeration unit. The heat insulator is arranged around the refrigerant supply tube. A set of the refrigerant supply tube, the refrigerant ejection tube and the heat insulator is arranged at a center of the cable unit substantially while the signal line is arranged around at least one of the refrigerant supply tube, the refrigerant ejection tube and the heat insulator.

2 Claims, 18 Drawing Sheets

ULTRASONIC PROBE AND ULTRASONIC DIAGNOSTIC APPARATUS

BACKGROUND OF THE INVENTION

1. Field of the Invention

The present invention relates to an ultrasonic probe and an ultrasonic diagnostic apparatus, and more particularly, to an ultrasonic probe and an ultrasonic diagnostic apparatus having a cooling system.

2. Description of the Related Art

An ultrasonic diagnostic apparatus for examining an object by transmitting ultrasonic waves to the object so as to use the reflected waves has been widely used in a medical field. An ultrasonic probe for transmitting/receiving ultrasonic waves is used by bringing its leading end in contact with the object, and the ultrasonic probe includes a plurality of transducers which generate ultrasonic waves while converting received ultrasonic waves into electric signals.

During operation of the ultrasonic diagnostic apparatus, not all the ultrasonic waves generated in the ultrasonic probe transmitting ultrasonic waves are transmitted to the object and part of them is absorbed in the transducers and converted into heat. When a circuit of a transmission/reception part for generating drive signals of ultrasonic waves and processing the received ultrasonic signals from the transducers in an ultrasonic diagnostic apparatus core connected to the ultrasonic probe is housed in the ultrasonic probe, electric power is consumed also in the circuit so as to generate heat.

The ultrasonic probe, as mentioned above, is used by bringing it in contact with a body surface of the object, it is necessary to design the ultrasonic probe so that the surface temperature does not exceed a predetermined temperature for its safety sake.

On the other hand, there is a method for improving the quality of ultrasonic images by increasing the power of transmitting ultrasonic waves so as to increase the S/N (signal to noise) ratio of the received ultrasonic waves. Although the power of transmitting ultrasonic waves has an upper limit for its safety, with increasing S/N ratio within a safe range, the larger S/N ratio can be obtained so as to improve the image quality.

However, if the power of transmitting ultrasonic waves is increased, the heat value in the ultrasonic probe is also increased so as to largely increase the surface temperature of the probe, thereby giving the object discomfort.

Recently, an ultrasonic probe capable of three-dimensional scanning has been developed, which includes two-dimensionally arranged transducers so as to three-dimensionally apply ultrasonic waves, and it has begun limited practical operations. In such an ultrasonic probe capable of three-dimensional scanning, the number of transducers increases in comparison with that of an ultrasonic probe capable of two-dimensional scanning in that transducers are unitarily arranged, so that when the circuit of the transmission/reception part in the ultrasonic diagnostic apparatus core is built in the probe, the scale of the circuit also becomes large.

Accordingly, in the ultrasonic probe capable of three-dimensional scanning, with increasing number of transducers and with increasing circuit scale, the heat value is increased, so that it is difficult to maintain the surface temperature at its front end lower than a predetermined level.

Then, an ultrasonic probe having a cooling mechanism using a refrigerant such as water has been proposed (see, for example, U.S. Pat. No. 5,560,362 or Japanese Patent Application (Laid-Open) No. 2003-38485). The proposed ultrasonic probe has a structure in that a refrigerant is circulated between an ultrasonic diagnostic apparatus core and the front end of the ultrasonic probe via a refrigerant tube attached to a cable of the ultrasonic probe so as to cool the ultrasonic probe. A cooling system, including a pump for passing the refrigerant to the ultrasonic probe and a radiator for cooling the refrigerant, is housed in a probe connector part connecting between the ultrasonic probe and the ultrasonic diagnostic apparatus core or in the ultrasonic diagnostic apparatus core.

FIG. 29 is a diagram showing an example of a structure of a conventional ultrasonic probe having a cooling mechanism. This ultrasonic probe 100 includes a probe unit 110, a compound cable unit 120 and a connector part 130. The probe unit 110 has a transducer part 111 and a heat-receiving part 112. The transducer part 111 transmits and receives ultrasonic waves to and from an object. The heat-receiving part 112 absorbs heat of the transducer part 111. The compound cable unit 120 communicates ultrasonic driving signals to the transducer part 111 and ultrasonic reception signals from the transducer part 111. The connector part 130 connects the compound cable unit 120 and an ultrasonic diagnostic apparatus core 200.

FIG. 30 is a diagram showing a section of the conventional compound cable unit 120 shown in FIG. 29. The compound cable unit 120 includes a multi-core cable 121, a refrigerant supply tube 122, a refrigerant ejection tube 123 and a coating 125. The multi-core cable 121 has signal lines 124 which communicate signals between the probe unit 110 and the connector part 130. The refrigerant supply tube 122 serves as a channel supplying a refrigerant cooled in the ultrasonic diagnostic apparatus core 200 to the heat-receiving part 112 of the probe unit 110 through the connector part 130. The refrigerant ejection tube 123 serves as a channel sending the refrigerant ejected from the heat-receiving part 112 to the ultrasonic diagnostic apparatus core 200 through the connector part 130. The coating 125 sticks and bundles the multi-core cable 121 in which each core has a circular section, the refrigerant supply tube 122 and the refrigerant ejection tube 123.

The compound cable unit 120 of the ultrasonic probe 100 having the cooling mechanism includes the refrigerant supply tube 122 and the refrigerant ejection tube 123 closely arranged outside the multi-core cable 121. Hence, due to the heat from the refrigerant ejection tube 123 for sending the refrigerant ejecting the heat of the heat-receiving part 112, the temperature of the refrigerant in the refrigerant supply tube 122 rises so as to reduce the cooling power of the heat-receiving part 112.

In the geometrical moment of inertia of the compound cable unit 120, as shown in FIG. 30, the geometrical moment of inertia about an axis XX of the length h in the moment direction (the diameter of the multi-core cable 121+a diameter close to that of the refrigerant supply tube 122 or the refrigerant ejection tube 123) is larger than those about axes YY, Y1Y1, and Y2Y2 of a length W in the moment direction close to the diameter of the multi-core cable 121, so that directional difference in bending easiness of the compound cable unit 120 is produced, deteriorating operationality of the ultrasonic probe.

On the other hand, in the ultrasonic probe housing a number of transducers or a number of transducers and a circuit board, the temperature of not only the front end of a probe unit but also of the entire probe unit is increased, so that a safety problem in handling the probe unit arises for an operator of the ultrasonic probe who gets hold it directly with a hand. Since the probe unit is provided with a endothirm part for absorbing the heat, the ultrasonic probe is increased in size, deteriorating the operationality.

When the cooling system is also assembled within the ultrasonic diagnostic apparatus core, it is necessary to circulate a refrigerant via a probe connector part, so that the cost of a connection mechanism for the refrigerant in between the ultrasonic diagnostic apparatus core and the probe connector part is increased while reliability in cooling power is difficult to be secured.

Furthermore, when a cooling system using a refrigerant is assembled within the ultrasonic probe including the probe connector part, since the space within the ultrasonic probe is small, it is difficult to achieve a cooling system with sufficient cooling power while securing reliability in cooling power.

In order to improve the cooling power, it is necessary to increase a radiator for radiating the heat of a refrigerant so as to cool the refrigerant. When a pump for circulating the refrigerant, the radiator, and a container for storing the refrigerant are housed within the probe connector part, the probe connector part is increased in size by the size of the large radiator. The pump for circulating the refrigerant, the radiator for radiating the heat of the refrigerant, and a radiator fan need to be built in the probe connector part, thereby also increasing the probe connector part in size. When increasing the cooling power in such a manner, the cooling system becomes large in size, so that it has been difficult to simultaneously satisfy the improvement of the cooling power and the miniaturizing the cooling system.

When cooling the ultrasonic probe by a cooling system incorporating the conventional technique, even when the temperature of the probe unit is not increased yet, the ultrasonic probe is cooled more than it needs, reducing energy efficiency.

SUMMARY OF THE INVENTION

The present invention has been made in light of the conventional situations, and it is the first object of the present invention to provide an ultrasonic probe which achieves improved cooling efficiency and operationality.

In addition, it is the second object of the present invention to provide an ultrasonic probe which can cool the entire probe unit thereof.

In addition, it is the third object of the present invention to provide an ultrasonic probe and an ultrasonic diagnostic apparatus having the ultrasonic probe which keep a sufficient cooling capacity with maintaining miniaturization.

The present invention provides an ultrasonic probe comprising: a probe unit having a transducer part and a heat-receiving part, the transducer part being configured to transmit and receive an ultrasonic wave, the heat-receiving part being configured to absorb heat generated from the transducer part; a refrigeration unit configured to refrigerate the heat-receiving part; and a cable unit having a signal line, a refrigerant supply tube, a refrigerant ejection tube and a heat insulator, the signal line being configured to communicate a signal between the transducer part and an ultrasonic diagnostic apparatus, the refrigerant supply tube being configured to supply a refrigerant from the refrigeration unit to the heat-receiving part, the refrigerant ejection tube being configured to send the refrigerant for ejecting heat of the heat-receiving part to the refrigeration unit, the heat insulator being arranged around the refrigerant supply tube; wherein a set of the refrigerant supply tube, the refrigerant ejection tube and the heat insulator is arranged at a center of the cable unit substantially while the signal line is arranged around at least one of the refrigerant supply tube, the refrigerant ejection tube and the heat insulator, in an aspect to achieve the first object.

The present invention also provides an ultrasonic probe comprising: a probe unit having a transducer part and a heat-receiving part, the transducer part being configured to transmit and receive an ultrasonic wave, the heat-receiving part being configured to absorb heat generated from the transducer part; a refrigeration unit configured to refrigerate the heat-receiving part; and a cable unit having a signal line, a refrigerant supply tube and a refrigerant ejection tube, the signal line being configured to communicate a signal between the transducer part and an ultrasonic diagnostic apparatus, the refrigerant supply tube being configured to supply a refrigerant from the refrigeration unit to the heat-receiving part, the refrigerant ejection tube being configured to send the refrigerant for ejecting heat of the heat-receiving part to the refrigeration unit; wherein one of the refrigerant supply tube and the refrigerant ejection tube is arranged at a center of the cable unit while an other tube includes sub-tubes arranged at equal intervals substantially in positions on a circle away from the one.

With the ultrasonic probes as described above, it is possible to reduce a temperature change of refrigerant in the refrigerant supply tube and bend the cable unit almost similarly to any direction, thus improving cooling efficiency and operationality of them.

The present invention also provides an ultrasonic probe comprising: a probe unit; a connector unit configured to communicate a signal with an ultrasonic diagnostic apparatus core; and a cable unit connecting the probe unit with the connector unit, wherein the probe unit includes: a probe case; a transducer configured to transmit and receive an ultrasonic wave to and from a object, the transducer being arranged in the probe case; a shield arranged in the probe case to surround inside the probe case; a heat conduction part arranged between the shield and the transducer to conduct heat form the transducer to the shield; and a endotherm part configured to absorb heat of the shield, in an aspect to achieve the second object.

The present invention also provides an ultrasonic probe comprising: a probe unit; a connector unit configured to communicate a signal with an ultrasonic diagnostic apparatus core; and a cable unit connecting the probe unit with the connector unit, wherein the probe unit includes: .a probe case; a transducer configured to transmit and receive an ultrasonic wave to and from a object, the transducer being arranged in the probe case; a circuit board connected to the transducer to perform at least one of generation of an ultrasonic driving signal to be given to the transducer and processing of an ultrasonic reception signal received from the transducer; a shield arranged in the probe case to surround inside the probe case; a heat conduction part arranged between the shield and the circuit board to conduct heat form the circuit board to the shield; and a endotherm part configured to absorb heat of the shield The present invention also provides an ultrasonic probe comprising: a probe unit; a connector unit configured to communicate a signal with an ultrasonic diagnostic apparatus core; and a cable unit connecting the probe unit with the connector unit, wherein the probe unit includes: a probe case; a transducer configured to transmit and receive an ultrasonic wave to and from a object, the transducer being arranged in the probe case; and a shield arranged in the probe case to surround the transducer to absorb heat from the transducer and shield the transducer from an electromagnetic wave The present invention also provides an ultrasonic probe comprising: a probe unit; a connector unit configured to communicate a signal with an ultrasonic diagnostic apparatus core; and a cable unit connecting the probe unit with the connector unit, wherein the probe unit includes: a probe case; a transducer configured to transmit and receive an ultrasonic wave to and from a object, the transducer being arranged in the probe case; a circuit board connected to the transducer to perform at least one of generation of an ultrasonic driving signal to be given to the transducer and processing of an ultrasonic reception signal received from the transducer; and a shield arranged in the probe case to surround the circuit board to absorb heat from the circuit board and shield the circuit board from an electromagnetic wave With the ultrasonic probes as described above, it is possible to absorb heat generated in the each probe unit by the shield case and the endotherm unit therein so as to operate the ultrasonic probes safely. In addition, the increase in size of the each probe can be suppressed so as to easily operate the ultrasonic probes.

The present invention also provides an ultrasonic probe comprising: an ultrasonic transmission and reception unit having an ultrasonic transducer, a heat-receiver and a housing case, the ultrasonic transducer transmitting and receiving an ultrasonic wave, the housing case housing the ultrasonic transducer and the heat-receiver; and a probe connector unit configured to connect the ultrasonic transmission and reception unit to an ultrasonic diagnostic apparatus core, wherein the probe connector unit includes: a radiator having refrigerant channels connected each other to radiate heat of a refrigerant passing through the refrigerant channels; a circulation part configured to circulate the refrigerant between the heat-receiver and the radiator; and a connector case housing the radiator and the circulation part, in an aspect to achieve the third object.

The present invention also provides an ultrasonic diagnostic apparatus comprising: the ultrasonic probe above-mentioned; and an image generating unit configured to generate image data in accordance with a signal acquired through transmission and reception of an ultrasonic wave by the ultrasonic probe.

With the ultrasonic probe and the ultrasonic diagnostic apparatus as described above, it is possible to keep a sufficient cooling capacity with maintaining miniaturization.

DESCRIPTION OF THE PREFERRED EMBODIMENTS

An ultrasonic probe according to embodiments of the present invention will be described with reference to the accompanying drawings.

1. First Embodiment

Figure 2:
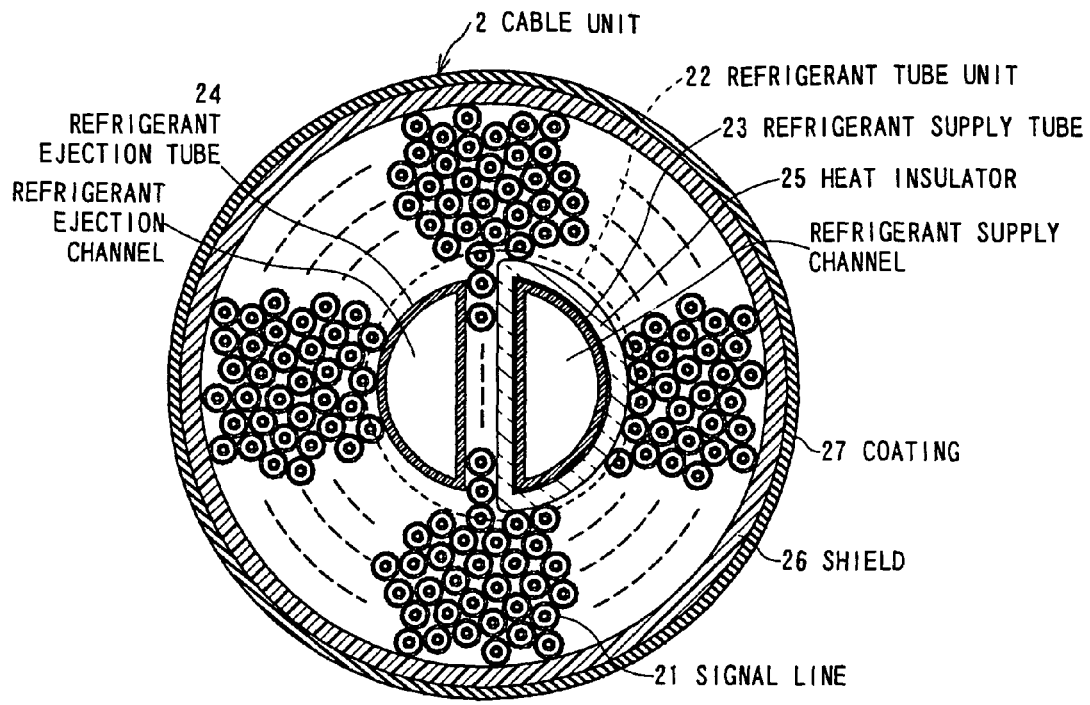
FIG. 2 is a diagram showing an example of a section of the cable unit shown in FIG. 1.
Figure 3:
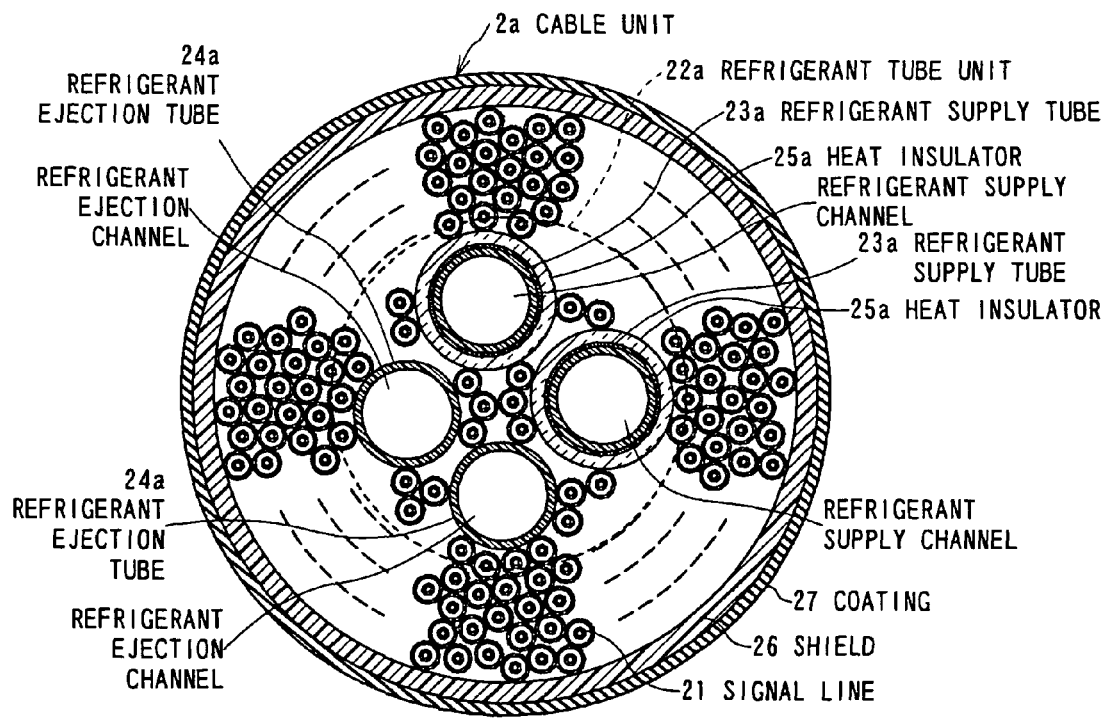
FIG. 3 is a sectional view showing a modified example of the cable unit shown in FIG. 1.

An ultrasonic probe according to a first embodiment of the present invention will be described with reference to FIGS. 1 to 3 and by exemplifying a case where a refrigerant for cooling a heat-receiving part of the ultrasonic probe and a cooler for air-cooling the refrigerant are provided.

Figure 1:
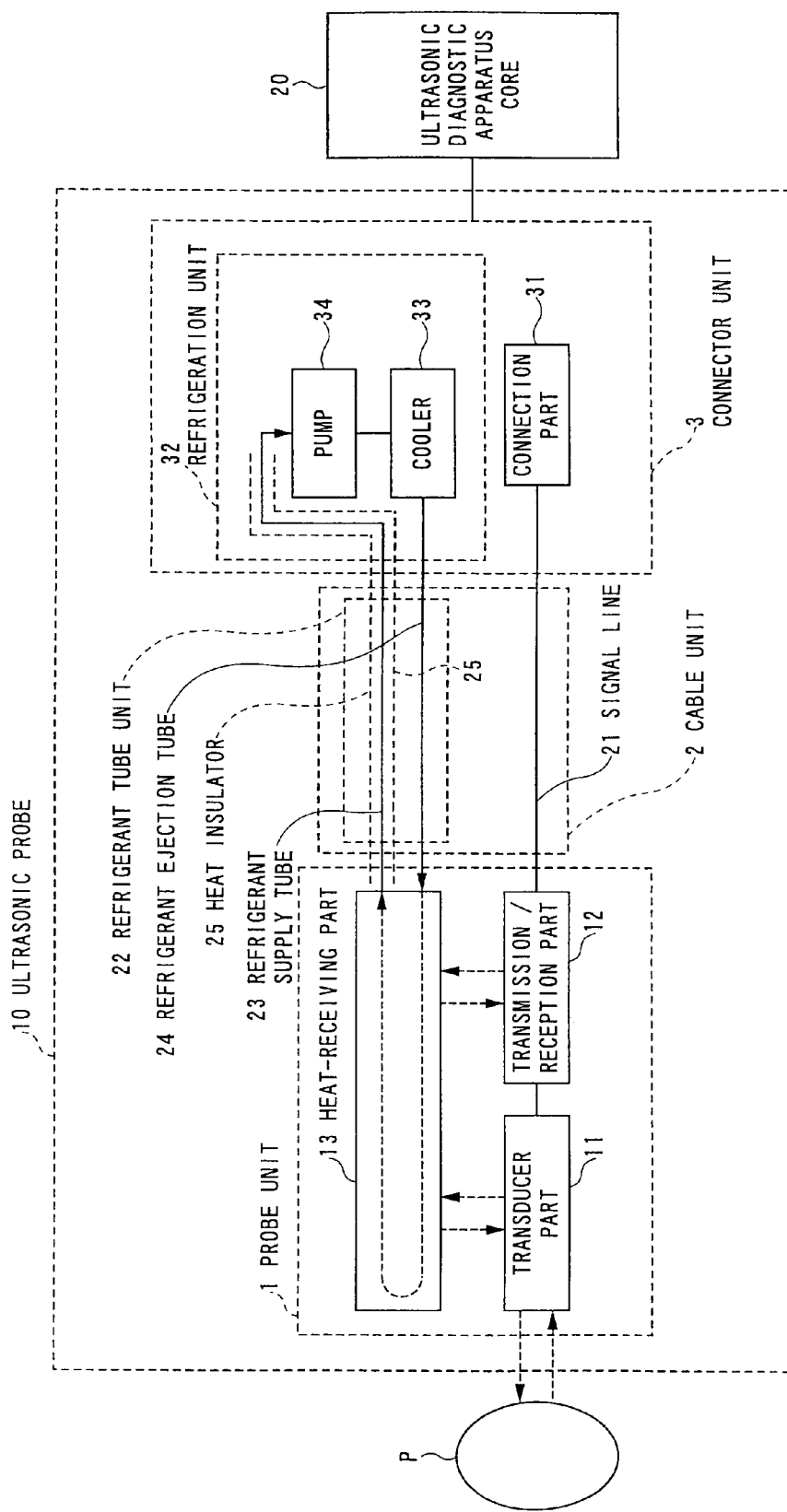
FIG. 1 is a block diagram showing an ultrasonic probe according to a first embodiment of the present invention.

FIG. 1 is a block diagram showing an ultrasonic probe according to the first embodiment of the present invention.

An ultrasonic probe 10 includes a probe unit 1, a cable unit 2 and a connector unit 3. The probe unit 1 transmits and receives ultrasonic waves to and from an object P. The cable unit 2 communicates signals for generating ultrasonic waves to the probe unit 1 and signals form the probe unit 1. The connector unit 3 which is detachable communicates signals for generating ultrasonic waves from an ultrasonic diagnostic apparatus core 20 to the cable unit 2 and signals from the cable unit 2 to the ultrasonic diagnostic apparatus core 20.

The probe unit 1 includes a transducer part 11, a transmission/reception part 12 and a heat receiving part 13. The transducer part 11 transmits ultrasonic waves to the object P and receives reflected waves from the object P. The transmission/reception part 12 performs processing to a signal from the cable unit 2 so as to generate an ultrasonic driving signal and performs processing to an ultrasonic reception signal from the transducer part 11. The heat receiving part 13 cools the transducer part 11 and the transmission/reception part 12.

The transducer part 11 includes a plurality (N pieces) of piezoelectric transducers, each made of an electro-acoustic transducer including a piezoelectric high-polymer material and a piezoelectric ceramics. The transducer part 11 converts an ultrasonic drive signal from a transmission circuit of the transmission/reception part 12 into a transmission ultrasonic wave during the transmitting of ultrasonic waves while converting the received ultrasonic wave into an ultrasonic reception signal during the receiving of ultrasonic waves.

The transmission/reception part 12 has a transmission circuit for generating the ultrasonic driving signal which allows the transducer part 11 to generate a transmission ultrasonic wave. The transducer part 11 includes a type capable of three-dimensional scanning for electronically applying an ultrasonic beam in a two- or three-dimensional direction by dividing the piezoelectric transducers to be two-dimensionally arranged and another type capable of two-dimensional scanning for electronically applying an ultrasonic beam in a two-dimensional direction by dividing the piezoelectric transducers to be single-dimensionally arranged. A case using the transducer part 11 capable of three-dimensional scanning will be described below.

The transmission circuit of the transmission/reception part 12 may include a pulsar for generating a driving pulse to drive N piezoelectric transducers so as to irradiate transmission ultrasonic waves to the object P; alternatively, in addition to the pulsar, it may include a transmission delay circuit for supplying a rate pulse to the pulsar, wherein a focusing delay time for focusing ultrasonic waves at a predetermined depth during the transmitting of ultrasonic waves and a deflecting delay time for transmitting ultrasonic waves in a three-dimensional scanning direction are fed to the rate pulse. Furthermore, in addition to the pulsar and the transmission delay circuit, the transmission circuit may also include a rate pulse generator for determining a repetition period (Tr) of an ultrasonic pulse to be irradiated to the object P. Any of these transmission circuits may be incorporated into the embodiment.

The transmission/reception part 12 may include a reception circuit for phase and add ultrasonic reception signals obtained from the transducer part 11. Alternatively, the transmission/reception part 12 may include both of the above-mentioned transmission circuit and the above-mentioned reception circuit. The reception circuit may include a preamplifier for amplifying a minute ultrasonic received signal from the transducer part 11 so as to have a sufficient S/N ratio; alternatively, in addition to the preamplifier, it may include a reception delay circuit for supplying a focusing delay time for focusing ultrasonic waves received from a predetermined depth to obtain a thin reception beam width and a deflecting delay time for setting the reception directivity of an ultrasonic beam in a three-dimensional scanning direction to the output of the preamplifier. Furthermore, in addition to the preamplifier and the reception delay circuit, the reception circuit may use an adder for adding received signals, which received from the reception delay circuit, on N channels from piezoelectric transducers.

The heat receiving part 13 includes an inlet for receiving a refrigerant (transmission refrigerant) from a cable unit 2, a refrigerant channel for passing the refrigerant, and an outlet for ejecting the refrigerant from the refrigerant channel to the cable unit 2, although these are not shown. Using the refrigerant (transmission refrigerant) fed from the cable unit 2, the transducer part 11 and the transmission/reception part 12 are cooled.

The cable unit 2 includes signal lines 21 and a refrigerant tube unit 22. The signal lines 21 communicate signals between the probe unit 1 and the connector unit 3. The refrigerant tube unit 22 works as a cyclical channel of a refrigerant between the probe unit 1 and the connector unit 3. The signal lines 21 are arranged around the refrigerant tube unit 22 positioned on the vicinity of the center inside the cable unit 2.

Each one end of the signal lines 21 is connected to the transmission/reception part 12 of the probe unit 1 while each other end of them is connected to the connector unit 3. The signal lines 21 transmit signals corresponding to the piezoelectric transducers of the transducer part 11 from the ultrasonic diagnostic apparatus core 20 to the transmission/reception part 12 of the probe unit 1 as well as ultrasonic reception signals corresponding to the piezoelectric transducers of the transducer part 11 from the transmission/reception part 12 to the connector unit 3.

The refrigerant tube unit 22 includes a refrigerant supply tube 23, a refrigerant ejection tube 24 and a heat insulator 25. The refrigerant supply tube 23 feeds a cooled refrigerant on supplying from the connector unit 3 to the heat receiving part 13 of the probe unit 1. The refrigerant ejection tube 24 feeds a refrigerant (refrigerant on ejecting) ejected from the heat receiving part 13 to the connector unit 3. The heat insulator 25 is arranged around the refrigerant supply tube 23.

The connector unit 3 includes a connection part 31 and a refrigeration unit 32. The connection part 31 communicates ultrasonic reception signals from the signal lines 21 of the cable unit 2 to the ultrasonic diagnostic apparatus core 20. The refrigeration unit 32 has a cooler 33 and a pump 34. The cooler 33 cools a refrigerant. The refrigeration unit 32 circulates a refrigerant in the ultrasonic probe 10.

One and of the connection part 31 is connected to the signal lines 21 of the cable unit 2 while the other end of it is detachably connected to the ultrasonic diagnostic apparatus core 20. The connection part 31 communicates signals for generating ultrasonic waves from the ultrasonic diagnostic apparatus core 20 to the cable unit 2 as well as ultrasonic reception signals from the cable unit 2 to the ultrasonic diagnostic apparatus core 20.

One end of the cooler 33 having a fan and a radiator is connected to the refrigerant supply tube 23 of the cable unit 2 via the pump 34 while the other end is connected to the heat receiving part 13 of the probe unit 1 via the refrigerant ejection tube 24 of the cable unit 2.

A refrigerant on ejecting from the heat receiving part 13 returns to the refrigeration unit 32 via the refrigerant ejection tube 24 while a refrigerant on supplying, cooled in the refrigeration unit 32, is fed to the heat receiving part 13 via the refrigerant supply tube 23

The powers for driving the refrigeration unit 32 and the pump 34 are supplied from the ultrasonic diagnostic apparatus core 20.

Then, a structure of the cable unit 2 will be described with reference to FIG. 2. FIG. 2 is a diagram showing an example of a section of the cable unit shown in FIG. 1. The cable unit 2 has a circular section. The refrigerant tube unit 22 is arranged in the vicinity of the center on the circular section. The signal lines 21 are arranged so that an entire space around the refrigerant tube unit 22 is filled by the signal lines. A shield 26 shields the signal lines 21. A coating 27 coats the shield 26 for insulating and protection.

The refrigerant tube unit 22 has a substantially circular section. The refrigerant tube unit 22 has the refrigerant supply tube 23, the refrigerant ejection tube 24 and the heat insulator 25. The refrigerant ejection tube 24 is close to the refrigerant supply tube 23. The heat insulator 25 is arranged around the refrigerant supply tube 23. The heat insulator 25 may contact with the refrigerant ejection tube 24 due to bent operation of the cable unit 2.

The refrigerant supply tube 23 and the refrigerant ejection tube 24 are made of a flexible material such as silicone rubber or a soft vinyl chloride resin. The cross-section of the refrigerant supply tube 23 has a semicircular periphery, and within the semicircular periphery, a nearly semicircular transmission refrigerant channel is provided. The refrigerant ejection tube 24 has a structure similar to that of the refrigerant supply tube 23, and is provided with an ejection refrigerant channel with the same cross-section area as that of the transmission refrigerant channel.

The heat insulator 25 is made of a tubular or tape-shaped heat-insulating and flexible material, such as a foamed plastic, and the refrigerant supply tube 23 is embraced or wrapped with the heat insulator 25 so that the heat insulator 25 has the same shape as that of the refrigerant supply tube 23.

According to the first embodiment, an ultrasonic probe 10 has been described in that a refrigerant for cooling the heat receiving part is air-cooled by the cooler; alternatively, the refrigerant may be cooled by a control circuit for temperature controlling the cooler having a Peltier element based on the signal from a thermometer provided in the heat receiving part.

Also, the ultrasonic probe 10 has the circuit of the transmission/reception part; however, the ultrasonic probe without the circuit of the transmission/reception part may also be incorporated in the embodiment.

Then, a modified example of the cable unit will be described with reference to FIG. 3. FIG. 3 is a sectional view showing a modified example of the cable unit shown in FIG. 1. The point of a cable unit 2a shown in FIG. 3 differing from the cable unit 2 shown in FIG. 2 is that two circular cross-sectional refrigerant supply tubes and two circular cross-sectional refrigerant ejection tubes are provided.

Refrigerant supply tubes 23a and refrigerant ejection tubes 24a of a refrigerant tube unit 22a, each being circular with the same outer and inner diameters, are arranged in the vicinity of the center of a cable unit 2a in contiguity with each other. The refrigerant tube unit 22a is provided with heat insulators 25a arranged around the refrigerant supply tubes 23a. The inside shape of the heat insulator 25a is same as the exterior shape of the refrigerant supply tube 23a. The heat insulators 25a are arranged close to the refrigerant ejection tubes 24a. In addition, the heat insulator 25a may be brought into contact with the refrigerant ejection tube 24a by the bending of the cable unit 2a.

Other than examples of the first embodiment, one refrigerant supply tube and one refrigerant ejection tube, each cross-sectional area of each channel being twice that of the refrigerant supply tube 23a or the refrigerant ejection tube 24a, may be arranged in the vicinity of the center of the cable unit, and a heat insulator may be provided around the refrigerant supply tube.

Also, 2N refrigerant supply tubes and 2N refrigerant ejection tubes, each cross-sectional area of each channel being 1/N times that of the refrigerant supply tube 23a or the refrigerant ejection tube 24a, may be arranged in the vicinity of the center of the cable unit.

As described above, in the ultrasonic probe 10 according to the first embodiment of the present invention, a cable unit with a circular cross-section includes signal lines, a refrigerant supply tube, a refrigerant ejection tube, and a heat insulator provided around the refrigerant supply tube, in which by arranging the refrigerant supply tube with a semicircular cross-section, the refrigerant ejection tube with the same cross-section as that of the refrigerant supply tube, and the heat insulator in the vicinity of the center of the cable unit, the temperature change of a refrigerant in the refrigerant supply tube is reduced while the geometrical moment of inertia of the cross-section of the cable unit is equalized about any axis so as to almost equalize the bending easiness in any direction of the cable unit, improving the cooling efficiency and the operability of the ultrasonic probe.

Also, at least one refrigerant supply tube with a circular cross-section and at least one refrigerant ejection tube with a circular cross-section are provided, in which by arranging the refrigerant supply tube, the refrigerant ejection tube, and a heat insulator provided around the refrigerant supply tube in the vicinity of the center of the cable unit, the temperature change of a refrigerant in the refrigerant supply tube is reduced while the geometrical moment of inertia of the cross-section of the cable unit is equalized about any axis so as to almost equalize the bending easiness in any direction of the cable unit, improving the cooling efficiency and the operability of the ultrasonic probe.

In addition, the present invention is not limited to the examples of the first embodiment. For example, when the temperature of the ejected refrigerant of the heat receiving part is high, the heat insulator may also be provided around the refrigerant ejection tube in the same way as that in the refrigerant supply tube.

2. Second Embodiment

An example of a cable unit of an ultrasonic probe according to a second embodiment of the present invention will be described below with reference to FIG. 4.

Figure 4:
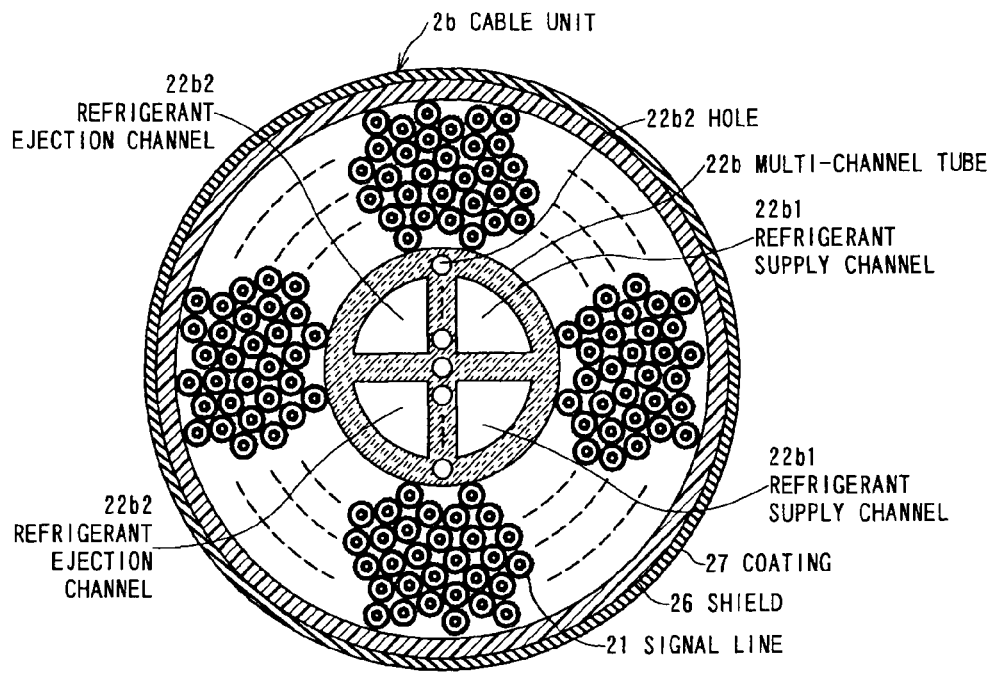
FIG. 4 is a sectional view showing a cable unit of an ultrasonic probe according to a second embodiment of the present invention.

FIG. 4 is a sectional view showing a cable unit of an ultrasonic probe according to the second embodiment of the present invention. The point of an ultrasonic probe according to a second embodiment shown in FIG. 4 differing from the ultrasonic probe according to the first embodiment shown in FIG. 2 is that instead of the refrigerant tube unit, a multi-channel tube having four independent channels is provided in the longitudinal direction.

The cross-section of a cable unit 2b is circular, and in the vicinity of the center of the section, a multi-channel tube 22b having a circular cross-section is arranged. The multi-channel tube 22b is made of a flexible and heat insulating material such as silicone rubber or a soft vinyl chloride resin, and has two refrigerant supply channels 22b1 and two refrigerant ejection channels 22b2 formed so as to equally divide the multi-channel tube 22b into four sectorial channel sections. Furthermore, a number of holes 22b2 formed in a separation wall between the refrigerant supply channels 22b1 and the refrigerant ejection channels 22b2 insulate the heat between the refrigerant supply channels 22b1 and the refrigerant ejection channels 22b2.

Signal lines 21 are arranged so that an entire space around the multi-channel tube 22b is filled by the signal lines. A shield 26 is arranged around the signal lines 21 for shielding them. A coating 27 coats the shield 26 for insulating and protection.

The multi-channel tube may have one refrigerant supply channel and one refrigerant ejection channel. It may also have the appropriate number of refrigerant supply or ejection channels.

As described above, in the ultrasonic probe according to the second embodiment of the present invention, a cable unit includes a multi-channel tube arranged in the vicinity of the center of the cable unit so as to have refrigerant supply channels and refrigerant ejection channels independently in the longitudinal direction, and furthermore, holes are formed in a separation wall between the refrigerant supply channels and the refrigerant ejection channels, and the cable unit is formed to have a circular cross-section, so that the temperature change of a refrigerant in the refrigerant supply tube is reduced while the geometrical moment of inertia of the cross-section of the cable unit is equalized about any axis so as to almost equalize the bending easiness in any direction of the cable unit, improving the cooling efficiency and the operability of the ultrasonic probe.

3. Third Embodiment

An ultrasonic probe according to a third embodiment of the present invention will be described below with reference to FIG. 5.

Figure 5:
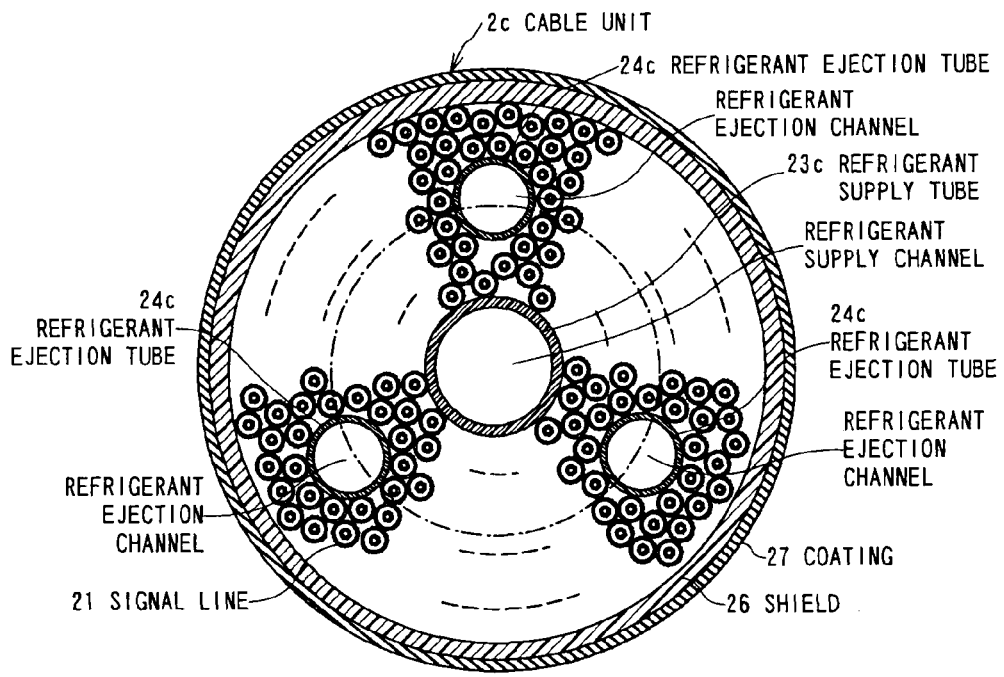
FIG. 5 is a sectional view showing a cable unit of an ultrasonic probe according to a third embodiment of the present invention.

FIG. 5 is a sectional view showing a cable unit of an ultrasonic probe according to the third embodiment of the present invention. The point of an ultrasonic probe according to a third embodiment shown in FIG. 5 differing from the ultrasonic probe according to the first embodiment shown in FIG. 2 is that refrigerant ejection tubes are arranged away from center of a cable unit.

A cable unit 2c has a circular section. A refrigerant supply tube 23c is arranged on a portion in the vicinity of center inside the cable unit 2c. Signal lines 21 are arranged around the refrigerant supply tube 23c. A shield 26 is arranged around the signal lines 21 for shielding them. A coating 27 coats the shield 26 for insulating and protection.

Three refrigerant ejection tubes 24c are arranged on a circle, which is located within portions close to an periphery of a cable unit 2c where signal lines 21 are arranged and apart from a refrigerant supply tube 23c, at equal intervals. In such a manner, by arranging the refrigerant ejection tubes 24c apart from the refrigerant supply tube 23c, the heat from the refrigerant ejection tubes 24c is conducted via the signal lines 21 with a small thermal conductivity, so that the temperature reduction of a refrigerant in the refrigerant supply tube 23c is decreased.

The cross-section of the refrigerant supply tube 23c is circular and within the tube, a circular refrigerant supply channel is formed. The cross-section of the refrigerant ejection tube 24c is a circle with both outer and inner diameters smaller than those of the refrigerant supply tube 23c. The cross-section area of a refrigerant ejection channel formed within the refrigerant ejection tube 24c is approximately one third of that of the refrigerant supply channel.

When the cross-section area of the refrigerant ejection channel of the refrigerant ejection tubes 24c is 1/N times (N is an integer of 4 or more) that of the circular refrigerant supply channel of the refrigerant supply tube 23c, N refrigerant ejection tubes 24c may be arranged at equal intervals. In addition, the refrigerant supply tube mentioned above may be used as the refrigerant ejection tube while the refrigerant ejection tubes may be used as the refrigerant supply tubes.

As described above, in the ultrasonic probe according to the third embodiment of the present invention, a cable unit includes a first refrigerant tube arranged in the vicinity of the center of the cable unit and a plurality of second refrigerant tubes each having a cross-sectional area smaller than that of the first refrigerant tube and arranged on a circumferential circle apart from the first refrigerant tube at equal intervals, and the cable unit is formed to have a circular cross-section, so that the temperature change of a refrigerant in the refrigerant supply tube is reduced while the geometrical moment of inertia of the cross-section of the cable unit is equalized about any axis so as to almost equalize the bending easiness in any direction of the cable unit, improving the cooling efficiency and the operability of the ultrasonic probe.

In addition, the present invention is not limited to the examples of the third embodiment, so that when the temperature of the ejected refrigerant of the heat receiving part is high, the heat insulator may also be provided around the refrigerant supply tube. Furthermore, around the refrigerant ejection tube, the heat insulator may also be provided.

Then, ultrasonic probes according to a fourth to a seventh embodiments of the present invention will be described below with reference to FIGS. 6 to 11.

Following ultrasonic probes according to fourth to seventh embodiments will be described so as to have a circuit board inside for transmitting/receiving ultrasonic waves; however, the present invention is not limited to these, so that an ultrasonic probe in case that the ultrasonic diagnostic apparatus core has the transmitting/receiving circuit board incorporates the invention.

4. Fourth Embodiment

Figure 6:
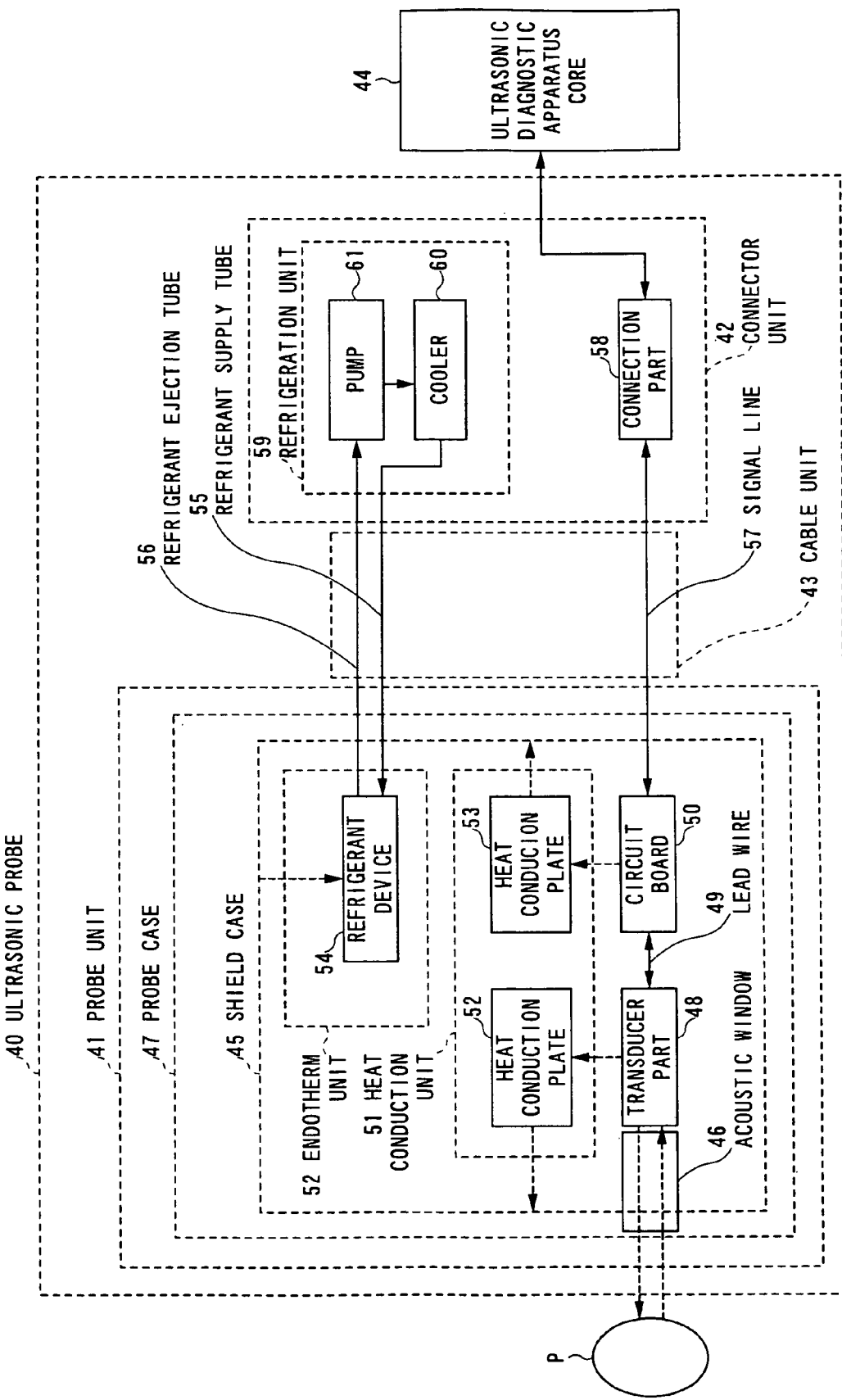
FIG. 6 is a block diagram showing an ultrasonic probe according to a fourth embodiment of the present invention.

FIG. 6 is a block diagram showing an ultrasonic probe according to the fourth embodiment of the present invention. A ultrasonic probe 40 includes a probe unit 41, a cable unit 43 and a connector unit 42. The probe unit 41 transmits and receives ultrasonic waves to and from an object P. One end of the cable unit 43 is connected to the probe unit 41 while the other end is connected to the connector unit 42. The connector unit 42 communicates signals with an ultrasonic diagnostic apparatus core 44.

Then, a structure of the probe unit 41 will be described with reference to FIG. 7.

Figure 7:
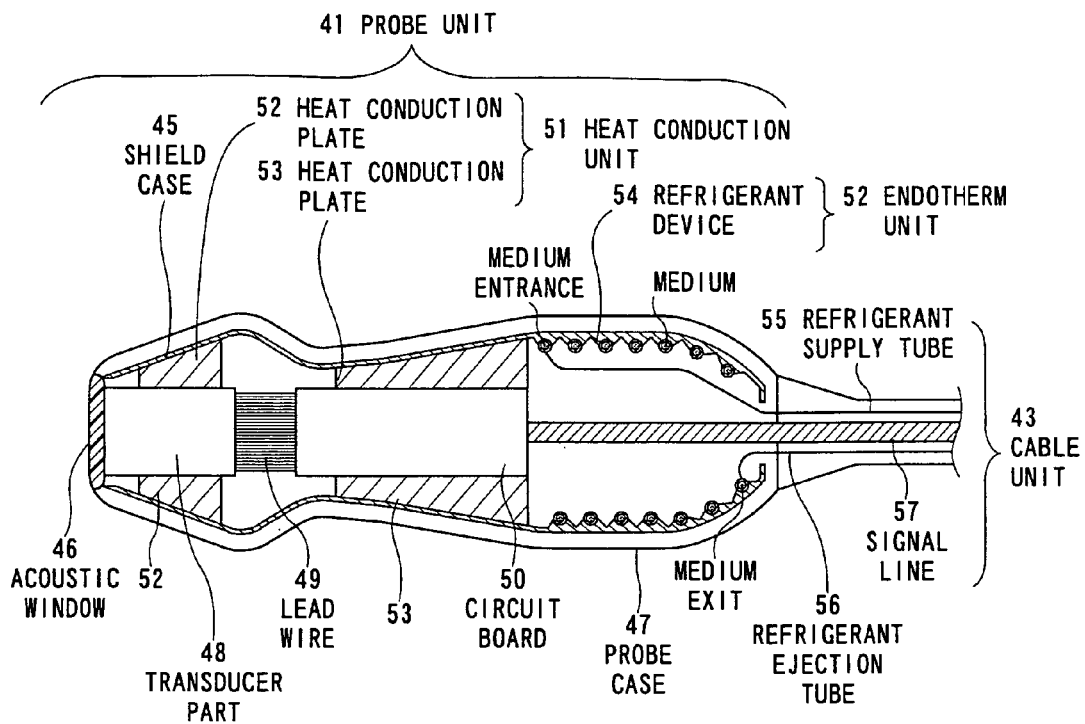
FIG. 7 is a diagram showing a structure of the probe unit shown in FIG. 6

FIG. 7 is a diagram showing a structure of the probe unit 41 shown in FIG. 6. The probe unit 41 includes a probe case 47 for holding a shield case 45 and an acoustic window 46 in order to prevent liquid from entering thereinto and insulate electrically from outside. For shielding electromagnetic waves, the shield case 45 is arranged over the almost entire inside of the probe case 47, and the acoustic window 46 is provided at the front end of the shield case 45 for allowing ultrasonic waves to transmit therethrough.

The probe case 47 is made of an electrically insulating plastic material so as to form an outer shell of the probe unit 41.

As mentioned above, the shield case 45, having substantially the same shape as that of the inside of the probe case 47, is made of a metallic material, such as copper, so as to shield electromagnetic waves as well as to have a high thermal conductivity. The shield case 45 includes a transducer part 48, a circuit board 50, a heat conduction unit 51 and an endotherm unit 52 therein. The transducer part 48 transmits and receives ultrasonic waves to and from an object P. The circuit board 50 communicates signals with the transducer part 48 using a lead wire 49. The heat conduction unit 51 conducts heat generated in the transducer part 48 and the circuit board 50. The endotherm unit 52 absorbs heat from the heat conduction unit 51 via the shield case 45.

The transducer part 48, although not shown, includes a plurality of (N) piezoelectric transducers, a backing material for holding these piezoelectric transducers as well as absorbing unnecessary ultrasonic waves generated from these piezoelectric transducers so as to suppress vibrations, and an acoustic coherent layer for improving a transmission efficiency of ultrasonic waves. On each one end face for transmitting/receiving ultrasonic waves to/from the object P of a plurality of the piezoelectric transducers, the acoustic coherent layer is bonded while on each other end face, a lead wire 49 is connected.

The transducer part 48 includes a type capable of three-dimensional scanning for electronically applying an ultrasonic beam in a three-dimensional direction by dividing the piezoelectric transducers to be two-dimensionally arranged and another type capable of two-dimensional scanning for electronically applying an ultrasonic beam in a two-dimensional direction by dividing the piezoelectric transducers to be single-dimensionally arranged. A case using the transducer part 11 capable of three-dimensional scanning will be described below.

The lead wire 49 is connected to a circuit including a flexible printed substrate. One end of this circuit is connected to the piezoelectric transducers of the transducer part 48 while the other end is connected to circuits, corresponding to the piezoelectric transducers, within the circuit board 50. On transmission of ultrasonic waves, the lead wire 49 transmits ultrasonic driving signals from the circuit board 50 to the transducer part 48 so as to be converted to ultrasonic waves to be transmitted to an object P. On the other hand, on reception of ultrasonic waves, the transducer part 48 receives ultrasonic waves reflected to the object P to convert to ultrasonic reception signals. The ultrasonic reception signals are transmitted from the transducer part 48 to the circuit board 50 via the lead wire 49.

The circuit board 50 has a transmission circuit and/or a reception circuit. The transmission circuit generates ultrasonic driving signals for allowing the transducer part 48 to transmit ultrasonic waves. The reception circuit performs processing to ultrasonic reception signals from the transducer part 48 to transmit the signals to the cable unit 43.

The transmission circuit of the circuit board 50 has various patterns. The transmission circuit of the circuit board 50 may include a pulsar for generating a driving pulse to drive N piezoelectric transducers so as to irradiate transmission ultrasonic waves to the object P; alternatively, in addition to the pulsar, it may include a transmission delay circuit for supplying a rate pulse to the pulsar, wherein a focusing delay time for focusing ultrasonic waves at a predetermined depth during the transmitting of ultrasonic waves and a deflecting delay time for transmitting ultrasonic waves in a three-dimensional scanning direction are fed to the rate pulse. Furthermore, in addition to the pulsar and the transmission delay circuit, the transmission circuit may also include a rate pulse generator for determining a repetition period (Tr) of an ultrasonic pulse to be irradiated to the object P.

The reception circuit of the circuit board 50 has also various patterns. The reception circuit of the circuit board 50 may include a preamplifier for amplifying a minute ultrasonic received signal from the transducer part 48 so as to have a sufficient S/N ratio; alternatively, in addition to the preamplifier, it may include a reception delay circuit for supplying a focusing delay time for focusing ultrasonic waves received from a predetermined depth to obtain a thin reception beam width and a deflecting delay time for setting the reception directivity of an ultrasonic beam in a three-dimensional scanning direction to the output of the preamplifier. Furthermore, in addition to the preamplifier and the reception delay circuit, the reception circuit may use an adder for adding received signals, which received from the reception delay circuit, on N channels from piezoelectric transducers.

On the other hand, the heat conduction unit 51 includes heat conduction plates 52 and 53. The conduction plates 52 conduct heat generated in the transducer part 48. The conduction plates 53 conduct heat generated in the circuit board 50.

The heat conduction plates 52 and 53 are made of a material with a high thermal conductivity such as copper and aluminum. Each one end of the heat conduction plates 52 is connected to the transducer part 48. Each one end of the heat conduction plates 53 is connected to the circuit board 50. Each other end of the heat conduction plates 52 and 53 is connected to the shield case 45.

The shield case 45 is provided for shielding electromagnetic waves as well as for conducting the heat from the heat conduction unit 51 to the endotherm unit 52.

The endotherm unit 52 includes a refrigerant device 54 made of a tubular material with a high thermal conductivity such as copper. The refrigerant device 54 is spirally installed between the circuit board 50 inside the shield case 45 and the cable unit 43 so as to be bonded. A medium entrance of the refrigerant device 54 is connected to a refrigerant supply tube 55 of the cable unit 43 while a medium exit of the refrigerant device 54 is connected to a refrigerant ejection tube 56 of the cable unit 43.

The refrigerant device 54 conducts the heat from the shield case 45 to a refrigerant such as water, which fed to therein from the refrigerant supply tube 55 and the refrigerant absorbing the heat is discharged into the refrigerant ejection tube 56.

As described above, the heat generated in the transducer part 48 and the circuit board 50 is conducted to the endotherm unit 52 via the heat conduction unit 51 and the shield case 45, both with a high thermal conductivity, so that the heat is absorbed by the endotherm unit 52 so as to cool the inside of the probe unit 41, thereby cooling the entire inside of the probe unit 41.

In addition, the heat generated in the transducer part 48 and the circuit board 50 is conducted to the endotherm unit 52 also via air within the shield case 45 so as to cool the inside of the probe unit 41 by the heat absorption to the endotherm unit 52.

Referring back to FIG. 6, the cable unit 43 includes signal lines 57, the refrigerant supply tube 55 and the refrigerant ejection tube 56. The signal lines 57 intermediate transmission and reception of signals between the probe unit 41 and the connector unit 42. The refrigerant supply tube 55 and the refrigerant ejection tube 56 serve a circulation channel for a refrigerant between the probe unit 41 and the connector unit 42.

Each one end of the signal lines 57 is connected to the circuit board 50 of the ultrasonic probe 40 while each other end is connected to the connector unit 42. The signal lines 57 transmit signals, which correspond to the piezoelectric transducers of the transducer part 48, for generating ultrasonic waves from the connector unit 42 to the circuit board 50 of the probe unit 41. The signal lines 57 also transmit ultrasonic reception signals, which correspond to the piezoelectric transducers of the transducer part 48, from the circuit board 50 of the probe unit 41 to the connector unit 42.

The refrigerant supply tube 55 is made of a flexible and heat-insulating material, such as silicone rubber or a soft vinyl chloride resin, with one end connected to a refrigerant inlet of the refrigerant device 54 in the endotherm unit 52 of the probe unit 41 and the other end connected to the connector unit 42. The refrigerant from the connector unit 42 is fed to the refrigerant device 54 of the probe unit 41 via the refrigerant supply tube 55.

The refrigerant ejection tube 56 is made of a flexible and heat insulating material such as silicone rubber or a soft vinyl chloride resin. One end of the refrigerant ejection tube 56 is connected to the medium exit of the refrigerant device 54 while the other end is connected to the connector unit 42. Then, the refrigerant from the refrigerant device 54 is fed to the connector unit 42 via the refrigerant ejection tube 56.

The connector unit 42 is detachably connected to the ultrasonic diagnostic apparatus core 44. The connector unit 42 includes a connection part 58 and a refrigerant unit 59. The connection part 58 connects the signal lines 57 of the cable unit 43 with the ultrasonic diagnostic apparatus core 44. The refrigerant unit 59 cools the refrigerant from the refrigerant ejection tube 56 of the cable unit 43.

One end of the connection part 58 is connected to the signal lines 57 of the cable unit 43 while the other end is connected to the ultrasonic diagnostic apparatus core 44. The connection part 58 transmits signals for generating ultrasonic waves from the ultrasonic diagnostic apparatus core 44 to the signal lines 57 as well as ultrasonic reception signals from the signal lines 57 to the ultrasonic diagnostic apparatus core 44.

The refrigerant unit 59 includes a cooler 60 and a pump 61. The cooler 60 cools the refrigerant from the refrigerant ejection tube 56. The pump 61 circulates the refrigerants in the cooler 60, the refrigerant supply tube 55 and the refrigerant ejection tube 56 of the cable unit 43 and the refrigerant device 54 of the probe unit 41.

The cooler 60 has a fan and a radiator. One end of the cooler 60 is connected to the refrigerant supply tube 55 of the cable unit 43 while the other end is connected to the pump 61. Then, the cooler 60 cools the refrigerant from the refrigerant ejection tube 56 so that cooled refrigerant is fed to the refrigerant supply tube 55.

One end of the pump 61 is connected to the cooler 60 while the other end is connected to the refrigerant ejection tube 56. The pump 61 sucks in the refrigerant from the refrigerant ejection tube 56 and feeds the refrigerant to the cooler 60.

The powers for driving the cooler 60 and the pump 61 are supplied from the ultrasonic diagnostic apparatus core 44 by attaching the connector unit 42 to the ultrasonic diagnostic apparatus core 44.

5. Fifth Embodiment

An ultrasonic probe according to the fifth embodiment of the present invention will be described with reference to FIG. 8.

Figure 8:
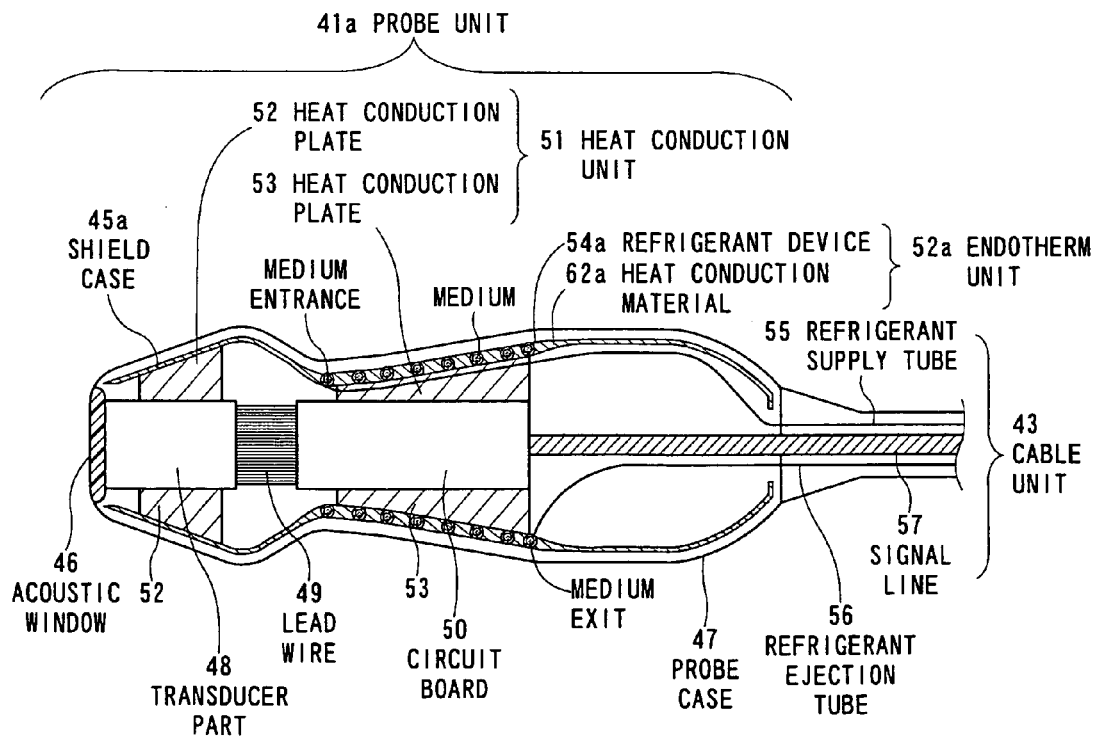
FIG. 8 is a structural drawing showing a probe unit of an ultrasonic probe according to a fifth embodiment of the present invention.

FIG. 8 is a structural drawing showing a probe unit of the ultrasonic probe according to the fifth embodiment of the present invention. The point of a probe unit 41a differing from the probe unit 41 is that whereas the endotherm unit 52 shown in FIG. 7 is provided between the circuit board 50 and the cable unit 43, an endotherm unit shown in FIG. 8 is arranged inside the shield case in the external periphery of the circuit board 50, and the endotherm unit is filled with a heat conduction material in addition to the refrigerant device. The probe unit 41a is used especially when the heat evolution from the circuit board 50 is large.

The shield case 45a of a probe 1a is made of a metallic material, such as copper, so as to shield electromagnetic waves as well as to have a high thermal conductivity, and includes a shield case outside metallic material (not shown) with the same shape as that of the inside of the probe case 47 and a shield case inside metallic material formed so as to sandwich the endotherm unit 52a provided between the inside of the shield case outside metallic material and the external periphery of the circuit board 50. On the inside of the shield case outside metallic material, on end of the shield case inside metallic material adjacent to an acoustic window 46 is bonded while the other end adjacent to the cable unit 43 is bonded.

The endotherm unit 52a includes the refrigerant device 54a made of a tubular material with a high thermal conductivity, such as copper, and a heat conducting material 62a, such as heat conduction gel or a heat conduction filler, and is arranged between the shield case outside metallic material 45a and the shield case inside metallic material of the shield case.

The refrigerant device 54a of the endotherm unit 52a is formed by spirally winding a tube, and is bonded on the internal surface of the shield case outside metallic material and the external surface of the shield case inside metallic material. Between windings of the refrigerant device 54a, a heat conduction material 62a is filled. A medium entrance of the refrigerant device 54a is connected to a refrigerant supply tube 55 of the cable unit 43 while a medium exit of the refrigerant device 54a is connected to a refrigerant ejection tube 56 of the cable unit 43.

When the cooling is performed with emphasis on the transducer part 48, the endotherm unit may be provided between the shield case outside metallic material and the external periphery of the transducer part 48 inside the shield case outside metallic material, so that the shield case made of the shield case inside metallic material formed by sandwiching the endotherm unit may be used.

6. Sixth Embodiment

Figure 9:
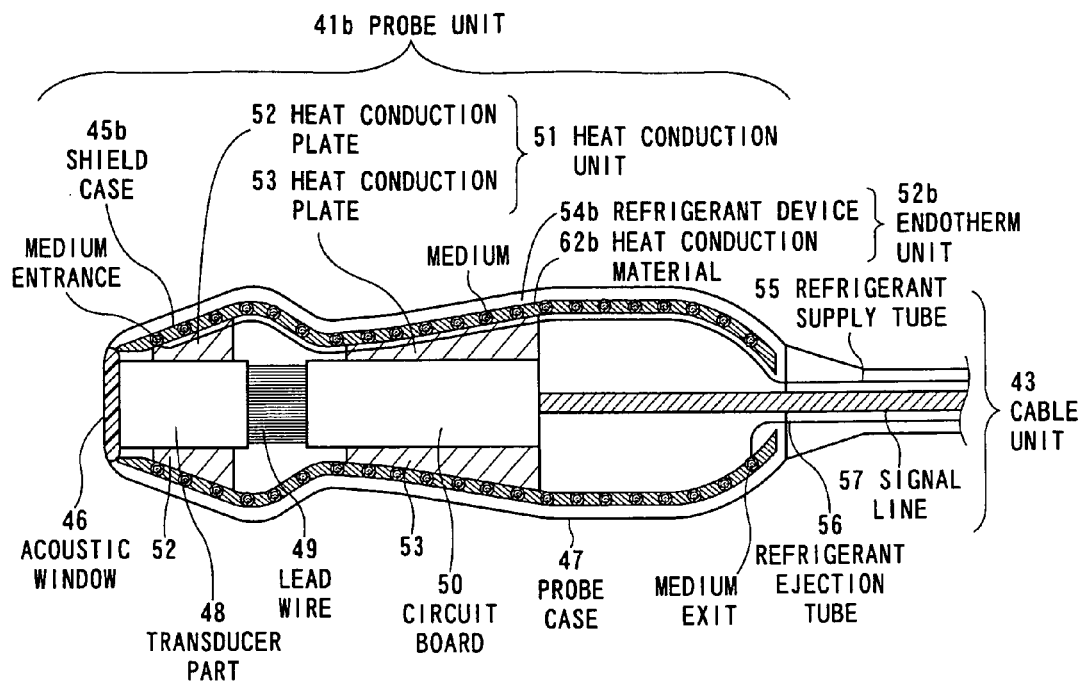
FIG. 9 is a structural drawing showing a probe unit of an ultrasonic probe according to a sixth embodiment of the present invention.

FIG. 9 is a structural drawing showing a probe unit of an ultrasonic probe according to the sixth embodiment of the present invention. The point of a probe unit 41b differing from the probe unit 41a shown in FIG. 8 is that whereas the endotherm unit 52a shown in FIG. 8 is provided around the circuit board 50, an endotherm unit 52b is arranged over the entire shield case. The probe unit 41b is used when the transducer part 48 and the circuit board 50 need to be further cooled.

The shield case 45b of the probe unit 41b is made of a metallic material, such as copper, so as to shield electromagnetic waves as well as to have a high thermal conductivity, and includes a shield case outside metallic material (not shown) with the same shape as that of the inside of the probe case 47 and a shield case inside metallic material formed so as to sandwich the endotherm unit 52b provided over the entire inside of the shield case outside metallic material. One ends of the shield case outside metallic material and the shield case inside metallic material in the vicinity of the acoustic window 46 are connected to each other. The other ends of them in the vicinity of the cable unit 43 are connected to each other.

The endotherm unit 52b includes the refrigerant device 54b made of a tubular material with a high thermal conductivity, such as copper, and a heat conducting material 62b, such as heat conduction gel or a heat conduction filler, and is arranged between the shield case outside metallic material 45a and the shield case inside metallic material of the shield case.

The refrigerant device 54b of the endotherm unit 52b is formed by spirally winding a tube, and is arranged in the whole between inside of the shield case outside metallic material and outside of the shield case inside metallic material. Between windings of the refrigerant device 54b, a heat conduction material 62a is filled. A medium entrance of the refrigerant device 54b is connected to a refrigerant supply tube 55 of the cable unit 43 while a medium exit of the refrigerant device 54b is connected to a refrigerant ejection tube 56 of the cable unit 43.

7. Seventh Embodiment

Figure 10:
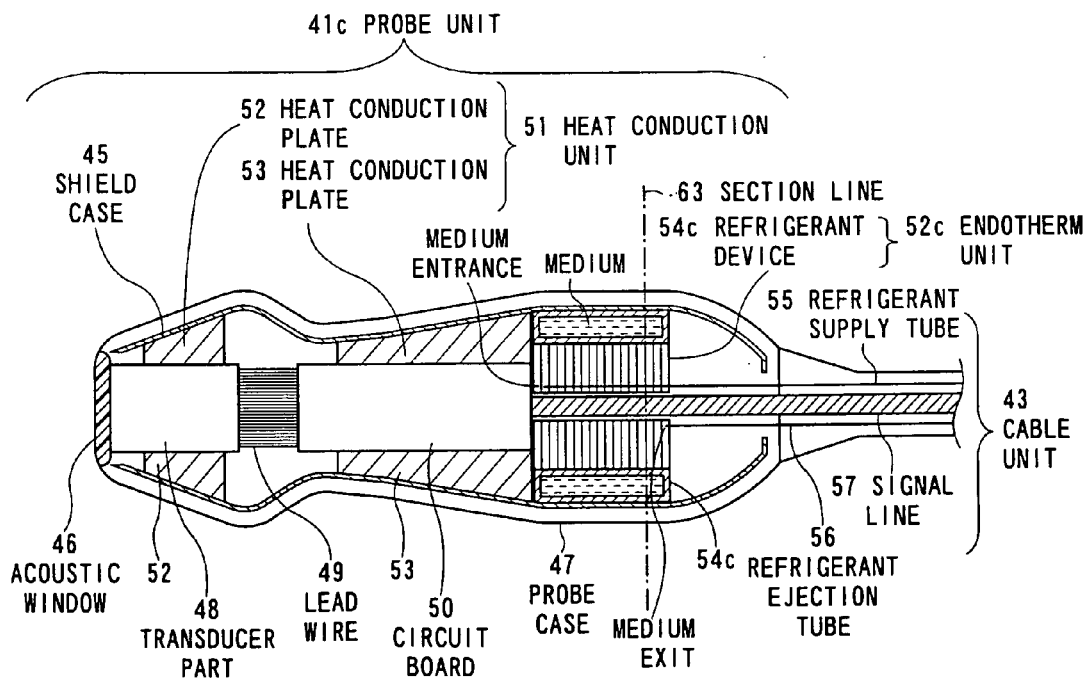
FIG. 10 is a structural drawing showing a probe unit of an ultrasonic probe according to a seventh embodiment of the present invention.

FIG. 10 is a structural drawing showing a probe unit of an ultrasonic probe according to the seventh embodiment of the present invention. The point of a probe unit 41c differing from the probe unit 41 shown in FIG. 7 is that whereas the endotherm unit 52 shown in FIG. 7 uses the tubular refrigerant device 54, an endotherm unit shown in FIG. 10 is provided with a refrigerant device made of a double tube having a refrigerant contained between tube walls.

An endotherm unit 52c is arranged at one end of the circuit board 50 arranged within the shield case 45 adjacent to the cable unit 43.

Then, a structure of the endotherm unit 52c will be described with reference to FIG. 11.

Figure 11:
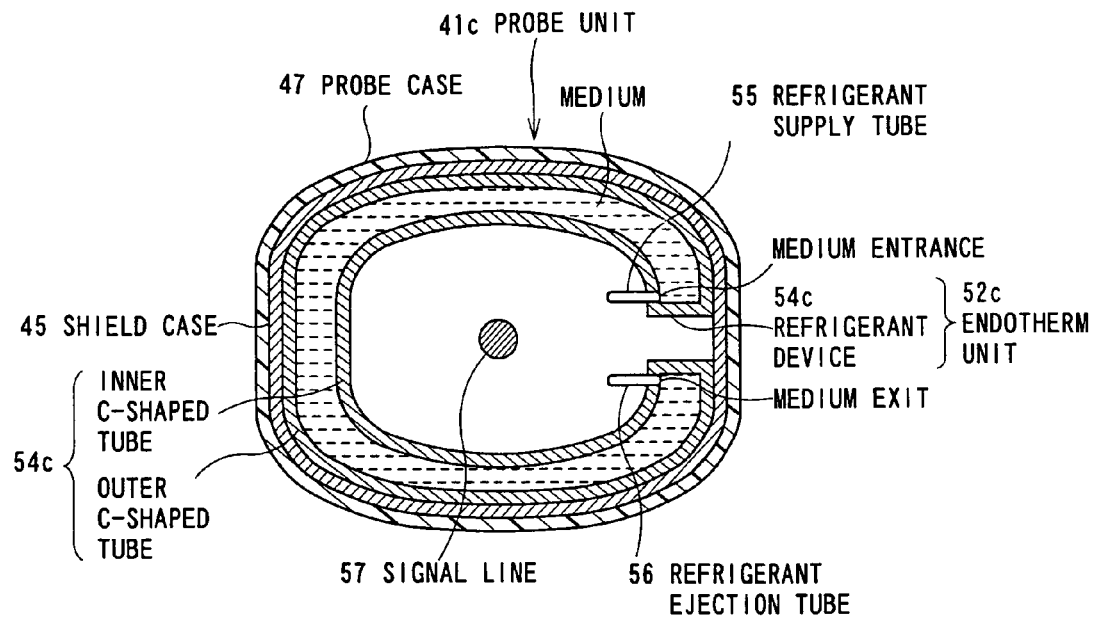
FIG. 11 is a view of the probe unit shown from the cable unit side of the section line of FIG. 10.

FIG. 11 is a view of the probe unit 41c shown from the cable unit 43 side of the section line 63 of FIG. 10. The endotherm unit 52c includes a tubular refrigerant device 54c having substantially the same external shape as the internal of a shield case 45c and a C-shaped section with a partial notch. Both ends of the C-shaped tube are covered with end members.

A medium entrance is provided in the vicinity of the notch of the C-shaped tube in the refrigerant device 54c. adjacent to the circuit board 50, and the medium entrance is connected to the refrigerant supply tube 55. Furthermore, a medium exit is provided in the vicinity of the notch in the refrigerant device 54c adjacent to the cable unit 43, and the medium exit is connected to the refrigerant ejection tube 56.

In each of the ultrasonic probes according to the fourth to seventh embodiments described above, by bonding the endotherm unit on the shield case within the probe unit, even when an operator of the ultrasonic probe holds the probe unit with a hand for a long time for operation, the entire probe unit is cooled because the heat is absorbed via the shield case covering the inside of the probe unit, maintaining reliable safety.

Also, since the increase in size of the probe unit is suppressed so as to easily operate the probe unit, the operability of the ultrasonic probe can be improved.

8. Eighth Embodiment

An ultrasonic probe according to the eighth embodiment of the present invention will be described with reference to FIGS. 12 and 13. A cable unit and a connector unit according to the eighth embodiment are substantially equivalent to the cable unit 43 and the connector unit 42 according to the fourth embodiment shown in FIG. 6 respectively. Therefore, the explanation of the cable unit and the connector unit according to the eighth embodiment is omitted.

Figure 12:
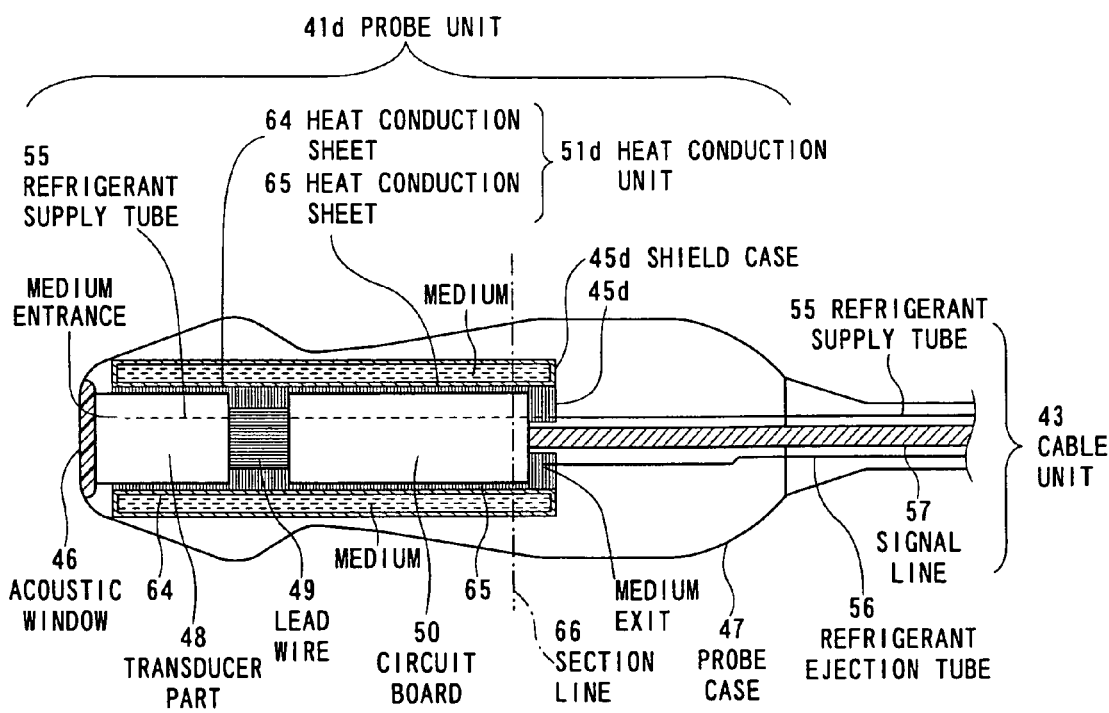
FIG. 12 is a structural drawing showing an ultrasonic probe according to an eighth embodiment of the present invention.
Figure 13:
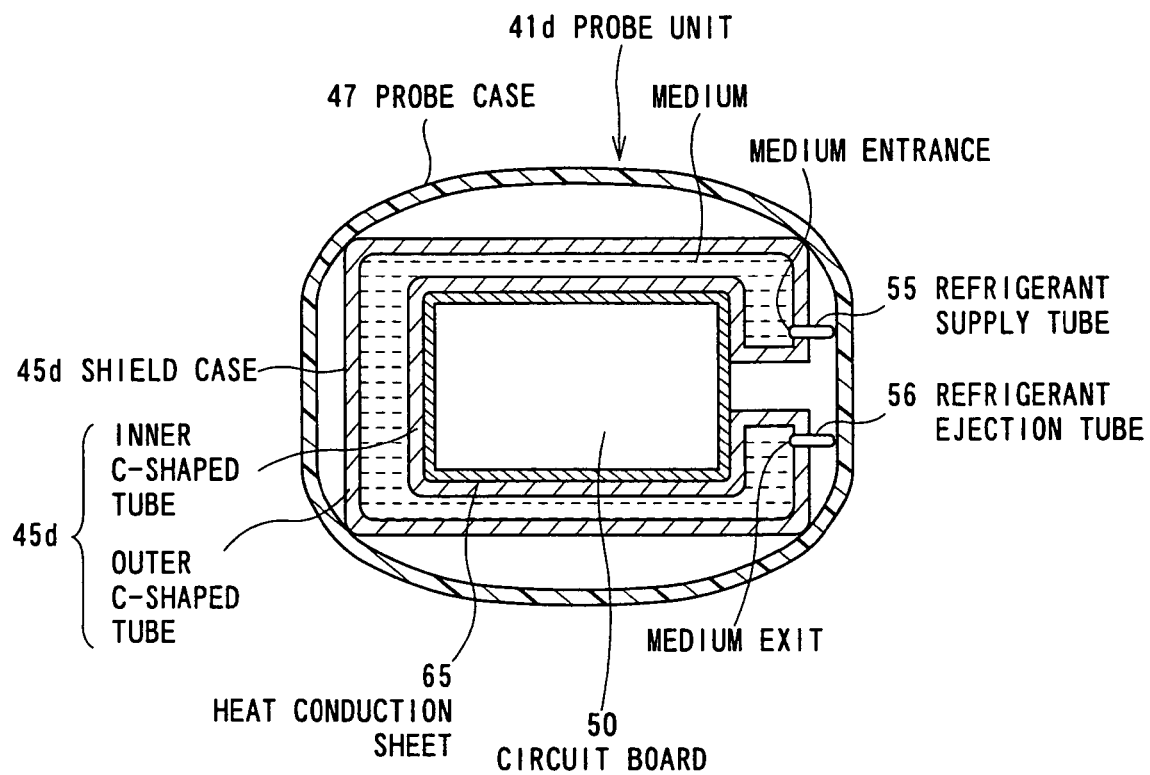
FIG. 13 is a sectional view of the probe unit shown from the cable unit side of the section line of FIG. 12.

FIG. 12 is a structural drawing showing an ultrasonic probe according to the eighth embodiment of the present invention. The point of an ultrasonic probe 1d according to the eighth embodiment shown in FIG. 12 differing from the ultrasonic probe 40 according to the fourth embodiment is that the shield case 45 and the endotherm unit 52 in the probe unit 41 shown in FIG. 6 are substituted for a shield case 45d while the heat conduction plates 52 and 53 of the heat conduction unit 51 are substituted for heat conduction sheets 64 and 65 of the heat conduction unit 51d.

The heat conduction unit 51d includes the heat conduction sheets 64 and 65 each having high heat conductivity. The heat conduction sheet 64 conducts heat generated in a transducer part 48 while the heat conduction sheet 65 conducts heat generated in a circuit board 50. The heat conduction sheets 64 and 65 are contacted to external faces of the transducer part 48 and the circuit board 50 respectively.

The shield case 45d is made of a metallic material, such as copper, so as to shield electromagnetic waves as well as to have a high thermal conductivity, and is arranged so as to abut external peripheries of the heat conduction sheets 64 and 65 of the transducer part 48 and the circuit board 50 for shielding electromagnetic waves as well as absorbing the heat from a heat conduction unit 51d.

A structure of the shield case 45d will be described with reference to FIG. 13. FIG. 13 is a sectional view of the probe unit 41d shown from the cable 43 unit side of the section line 66 of FIG. 12.

The shield case 45d has two tubes (an inner C-shaped tube and an outer C-shaped tube) combined each other. The inner C-shaped tube has a section of which internal shape is substantially the same as that of external of the transducer part 48 and the circuit board 50 as well as a partially notch forming C-shape. The outer C-shaped tube is contacted with the inner C-shaped tube so as to form space between outside of the inner C-shaped tube and inside of the outer C-shaped tube.

Both ends of the outer C-shaped tube and the inner C-shaped tube are covered with end plates, and furthermore, by covering two notch surfaces formed by the notches of the outer C-shaped tube and the inner C-shaped tube with plates, the shield case 45d is formed.

A medium entrance is provided in the notch of the outer C-shaped tube adjacent to the transducer part 48 of the shield case 45d, and the medium entrance is connected to one end of the refrigerant supply tube 55. Furthermore, a medium exit is provided in the notch of the outer C-shaped tube of the shield case 45d adjacent to the cable unit 43, and the medium exit is connected to one end of the refrigerant ejection tube 56.

In the ultrasonic probe according to the eighth embodiment, the transducer part and the circuit board are surrounded within the probe case, by the shield case which shields electromagnetic waves as well as to absorb the heat from the transducer part and the circuit board. Thus, the entire probe unit is cooled, maintaining reliable safety and improving the operationality of the ultrasonic probe.

Also, since the increase in size of the probe unit is suppressed so as to easily operate the probe unit, the operationality of the ultrasonic probe can be improved.

Then, ultrasonic probes and ultrasonic diagnostic apparatuses having the ultrasonic probes according to a ninth to fourteenth embodiments of the present invention will be described with reference to FIGS. 14 to 28.

9. Ninth Embodiment

9-1. Constitution

Figure 14:
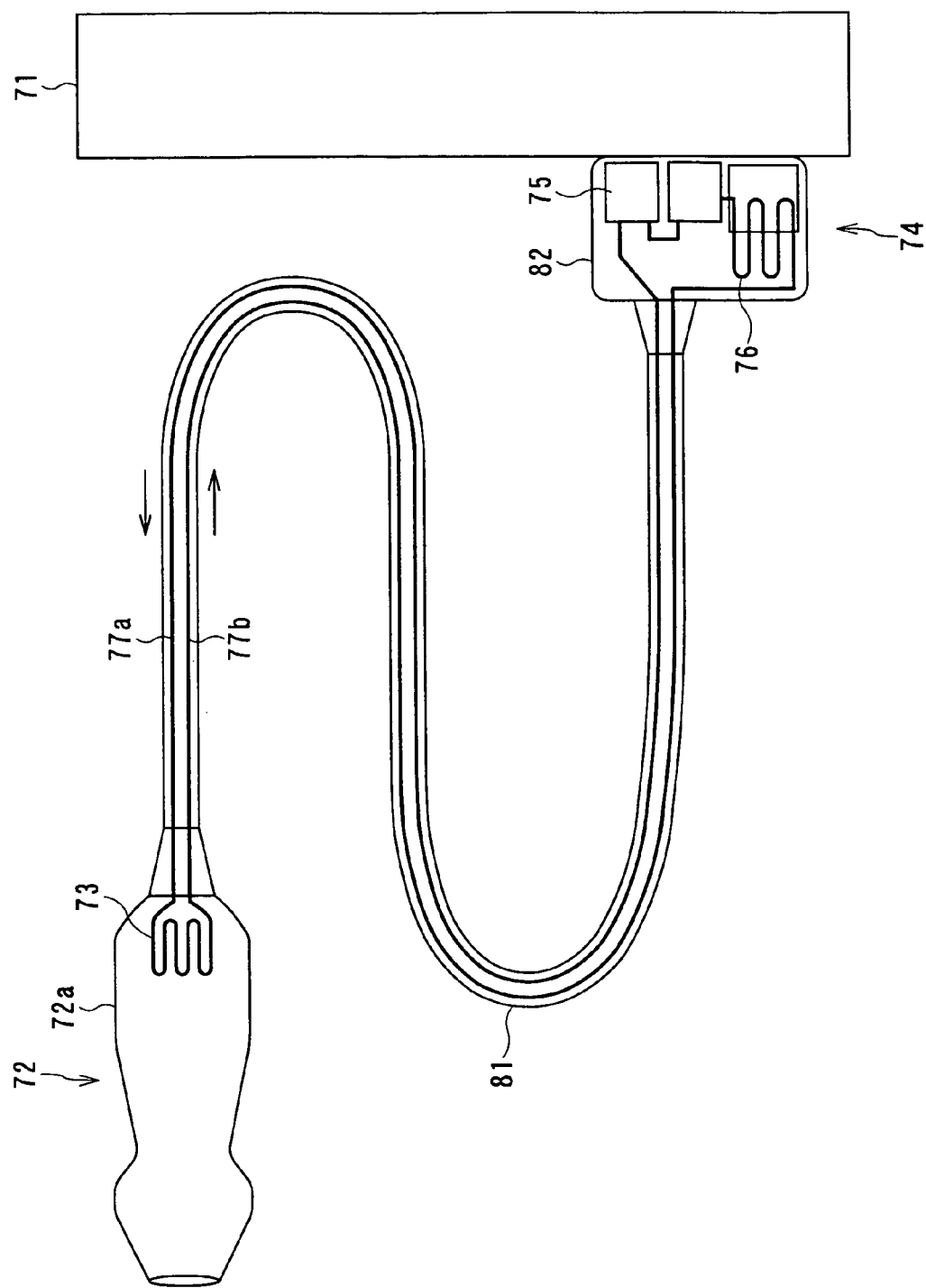
FIG. 14 is a diagram showing a summary structure of an ultrasonic probe and a whole ultrasonic diagnostic apparatus according to a ninth embodiment of the present invention.

Structures of an ultrasonic probe and an ultrasonic diagnostic apparatus having the ultrasonic probe according to the ninth embodiment of the present invention will be described with reference to FIGS. 14 to 17. FIG. 14 is a diagram showing a summary structure of an ultrasonic probe and a whole ultrasonic diagnostic apparatus according to the ninth embodiment of the present invention.

An ultrasonic diagnostic apparatus includes an ultrasonic diagnostic apparatus core 71 and an ultrasonic probe as shown in FIG. 14. The ultrasonic probe includes a probe unit 72, a cable 81 and a probe connector part 74. The probe unit 72 has piezoelectric transducers transmitting and receiving ultrasonic waves. The ultrasonic probe is detachably connected to the ultrasonic diagnostic apparatus core 71 by the probe connector part 74.

The probe unit 72 receives a high-frequency voltage signal from the ultrasonic diagnostic apparatus core 71 via the probe connector part 74 and the cable 81, and converts the signal into an ultrasonic signal with a piezoelectric transducer (not shown) so as to be transmitted to an object. Then, the reflected signal from the object is received as an echo signal so as to convert it into an electric signal by a piezoelectric effect of the piezoelectric transducer (not shown), and the electric signal is transmitted to the ultrasonic diagnostic apparatus core 71 via the cable 81 and the probe connector part 74. The probe unit 72 corresponds to "an ultrasonic transmission/reception part" of the present invention.

The ultrasonic diagnostic apparatus core 71 includes a signal processing circuit and a DSC (digital scan converter) circuit for generating image data. The signal processing circuit has a B mode processing system, a Doppler mode processing system and a color mode processing system. The B mode processing system performs envelope detection, logarithmic compression, intensity modulation and so forth. The Doppler mode processing system performs quadrature detection, extraction of Doppler deflected phase component, filter processing, FFT (fast Fourier transform) processing and so forth. The color mode processing system performs quadrature detection, filter processing, auto-correlation operation processing, flow-velocity/dispersion operation processing and so forth.

The cable 81 bundled with a plurality of signal lines (not shown) leads the signal lines (not shown) into the probe unit 72 from the probe connector part 74. The cable 81 is drawn into a housing case 72a of the probe unit 72 through an opening opened at the rear of the housing case 72a, and is fastened not to come off with a metallic cable cramp inside the housing case 72a.

The plurality of signal lines (not shown) are electrically connected inside the housing case 72a of the probe unit 72 to a plurality of signal lines of a flexible printed board and a resin substrate having electric circuits mounted thereon (both not shown).

A heat receiving part 73 for cooling the probe unit 72 is arranged in the housing case 72a the probe unit 72. The heat receiving part 73 made of a metal such as copper (Cu) or aluminum (Al) has a shape of a curved hollow tube. By circulating a refrigerant, such as water, to the inside of the heat receiving part 73, the probe unit 72 is cooled. The probe connector part 74 has a pump 75 and a radiator 76 as main elements in a connector case 82. The radiator 76 is made of a metal such as copper (Cu) or aluminum (Al). The structure of the radiator 76 will be described later in detail. Into the cable 81, tubular refrigerant tubes 77a and 77b are inserted. In addition, the pump 75 corresponds to "a circulation part" of the present invention.

With the pump 75 built in the probe connector part 74, a refrigerant is circulated via the refrigerant tubes 77a and 77b housed in the cable 81. By discharging the refrigerant with the pump 75, the refrigerant is fed to the heat receiving part 73 in the probe unit 72 from the probe connector part 74 via the refrigerant tube 77a. The heat receiving part 73 absorbs the heat generated in the probe unit 72 (the heat generated in the piezoelectric transducer, for example) so as to conduct it to the refrigerant. By the heat conduction from the heat receiving part 73 to the refrigerant in such a manner, the temperature of the probe unit 72 is decreased. On the other hand, by receiving the heat from the heat receiving part 73, the temperature of the refrigerant is increased.

By sucking the refrigerant with the pump 75, the refrigerant is sucked to the probe connector part 74 from the probe unit 72 via the refrigerant tube 77b. The refrigerant sucked by the pump 75 is delivered to the radiator 76 in the probe connector part 74. With the radiator 76, the heat of the refrigerant is radiated outside so as to cool the refrigerant, and the refrigerant is again discharged to the probe unit 72 by the refrigerant with the pump 75. By repeating this series of processes, the probe unit 72 is cooled.

Figure 15:
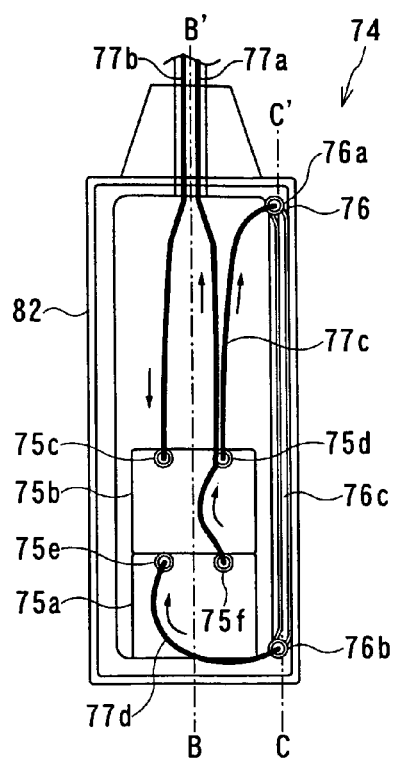
FIG. 15 is a front view of the probe connector part shown in FIG. 14.
Figure 16:
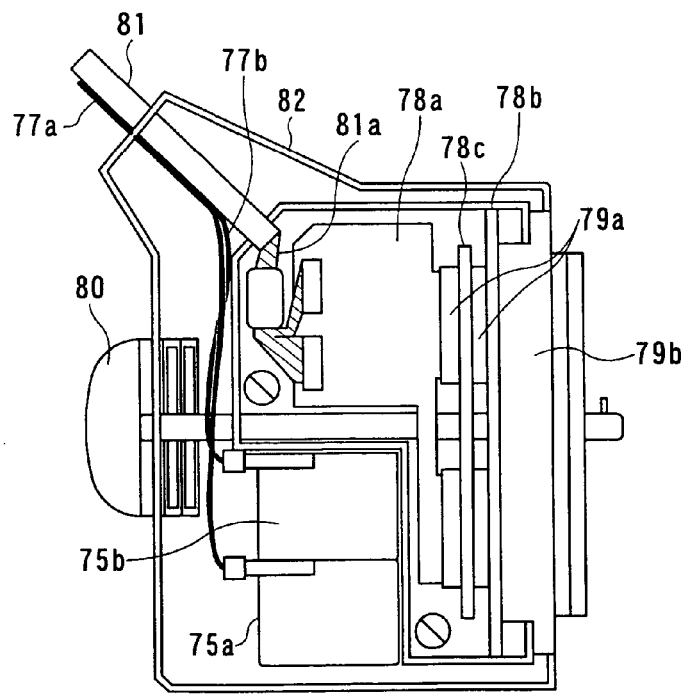
FIG. 16 is a sectional view of the probe connector part along the line segment B-B' shown in FIG. 15.
Figure 17:
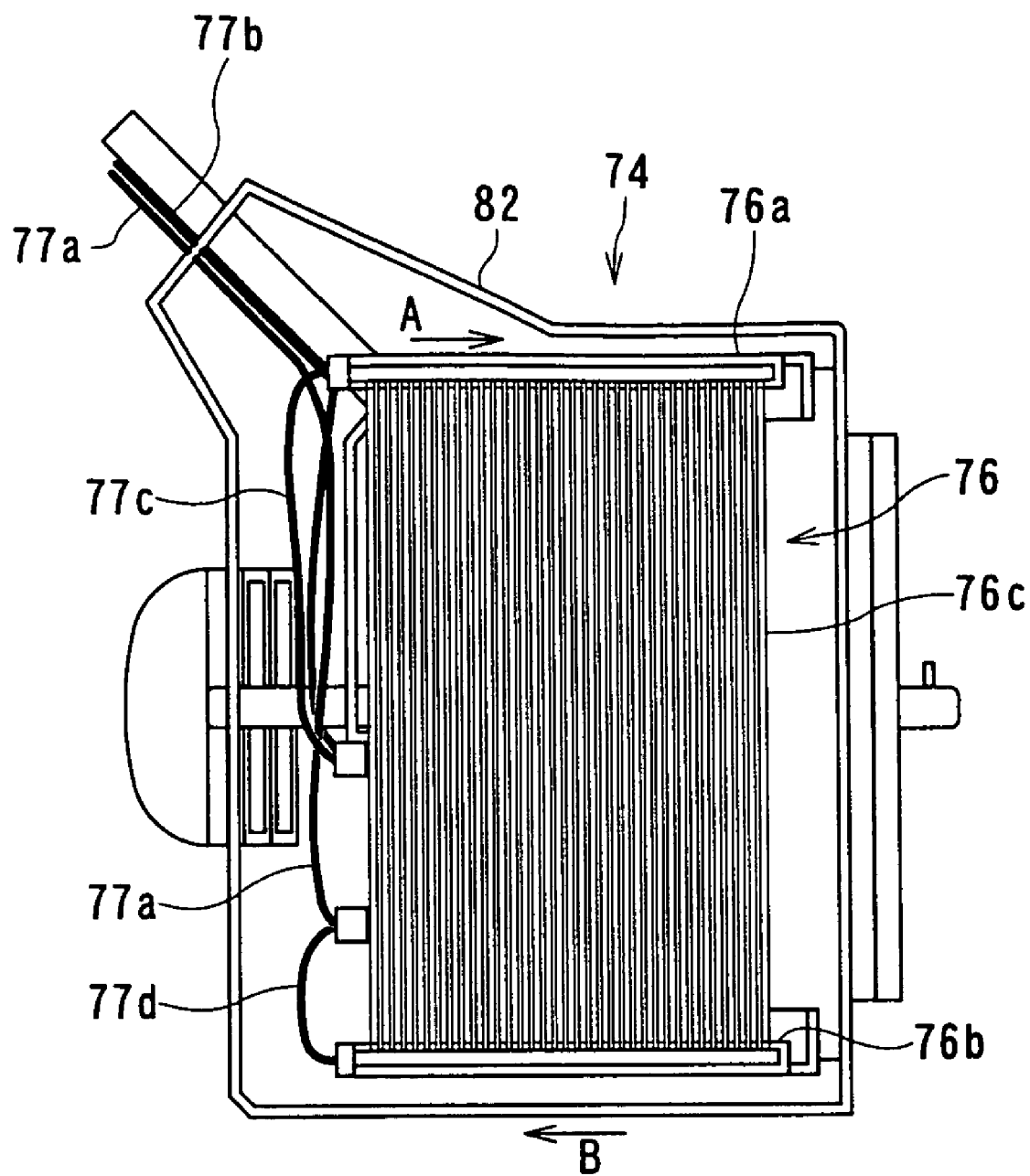
FIG. 17 is a sectional view of the probe connector part along the line segment C-C' shown in FIG. 15.

Now, a detailed structure of the probe connector part 74 will be described with reference to FIGS. 15 to 17. FIG. 15 is a front view of the probe connector part 74 shown in FIG. 14. FIG. 16 is a sectional view of the probe connector part 74 along the line segment B-B' shown in FIG. 15. FIG. 17 is a sectional view of the probe connector part 74 along the line segment C-C' shown in FIG. 15.

As shown in FIGS. 15 and 16, the probe connector part 74 includes a feed pump 75a for feeding the refrigerant to the probe unit 72 and a suction pump 75b for sucking the refrigerant from the probe unit 72 arranged within the connector case 82. Furthermore, the probe connector part 74 includes the radiator 76 for cooling the refrigerant. According to the ninth embodiment, both the feed pump 75a and the suction pump 75b are provided; alternatively, with one pump, the refrigerant may be fed/sucked.

One end of the refrigerant tube 77a is connected to the feed pump 75a while one end of the refrigerant tube 77b is connected to the suction pump 75b. The other ends of the refrigerant tubes 77a and 77b built in the cable 81 are connected to the heat receiving part 73 in the probe unit 72. The feed pump 75a feeds the refrigerant to the heat receiving part 73 in the probe unit 72 via the refrigerant tube 77a while the suction pump 75b sucks the refrigerant from the probe unit 72 via the refrigerant tube 77b.

The feed pump 75a is provided with a flow regulating valve 76a for regulating the flow rate of the refrigerant fed to the heat receiving part 73 of the probe unit 72 via the refrigerant tube 77a. By changing the drive voltage applied to the feed pump 75a, the flow rate of the refrigerant fed from the feed pump 75a can be regulated. By adjusting the valve travel of the flow regulating valve (aperture size), the flow rate of the refrigerant fed from the feed pump 75a to the refrigerant tube 77a can also be regulated.

One end of a refrigerant tube 77c is connected to the suction pump 75b while the other end is connected to a header pipe 76a of the radiator 76. The suction pump 75b sucks the refrigerant from the heat receiving part 73 of the ultrasonic probe 2 via the refrigerant tube 77b to feed the refrigerant sucked to the radiator 76 via the refrigerant tube 77c. Furthermore, one end of a-refrigerant tube 77d is connected to the feed pump 75a while the other end is connected to a header pipe 76b of the radiator 76. The feed pump 75a sucks the refrigerant from the radiator 76 to feed the refrigerant sucked to the heat receiving part 73 of the ultrasonic probe 2 via the refrigerant tube 77a.

Figure 18:
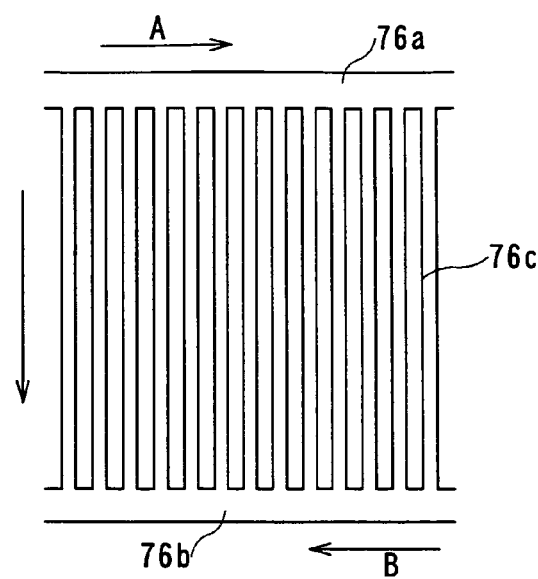
FIG. 18 is a diagram showing a structure of the endotherm unit shown in FIG. 17.

Now, a structure of the radiator 76 cooling the refrigerant will be described with reference to FIGS. 17 to 19. FIG. 18 is a diagram showing a structure of the radiator 76 shown in FIG. 17.

As shown in FIGS. 17 and 18, in the radiator 76, a number of hollow refrigerant channels 76c are juxtaposed and connected together. Since such a number of refrigerant channels 76c are juxtaposed and connected together, the radiator 76 has a plate-like shape as a whole. One ends of the refrigerant channels 76c are connected together with a header pipe 76a extending in the juxtaposing direction and the other ends are connected together with a header pipe 76b extending in the juxtaposing direction. By passing the refrigerant through the inside of the refrigerant channels 76c, heat of the refrigerant is radiated outside so as to cool the refrigerant.

By juxtaposing such a number of the refrigerant channels 76c to be connected together, the surface area (radiation area) of the radiator 76 is increased, so that the rate of the surface area to the size of the radiator 76 is increased. That is, while the surface area (radiation area) is increased, the radiator 76 can be decreased in size, so that even when the radiator 76 is decreased in size, the radiation efficiency can be improved. Since the radiator 76 can be decreased in size, the connector case 82 for housing the radiator 76 can be miniaturized, resulting in the miniaturization of the ultrasonic probe.

By closely attaching the plate-like radiator 76 on the internal surface of the connector case 82, the heat radiated from surfaces of the plural refrigerant channels 76c of the radiator 76 is liable to be radiated outside. That is, because the heat radiated from the radiator 76 is directly conducted to the connector case 82, the heat is easily radiated outside the connector case 82, cooling the refrigerant efficiently.

Furthermore, since the plate-like radiator 76 is arranged along the internal surface of the connector case 82, the space occupied by the radiator 76 can be reduced in the connector case 82. Thereby, while the radiation efficiency with the radiator 76 being improved, the ultrasonic probe can be miniaturized.

Inside the connector case 82, circuit boards 78a, 78b, and 78c are arranged, to which one ends of a plurality of signal lines 81a are connected. The other ends are connected to the probe unit 72, so that an electric signal is transmitted to the probe unit 72 via the signal lines 81a while an electric signal is received from the probe unit 72. A plurality of the signal lines 81a are bundled with the cable 81 and are led into the probe unit 72 from the probe connector part 74.

The probe connector part 74 is connected to the ultrasonic diagnostic apparatus core 71 with a DL connector 79b. A connector locking structure 80 locks up the probe connector part 74 on the ultrasonic diagnostic apparatus core 71. Consequently, the ultrasonic probe is detachably connected to the ultrasonic diagnostic apparatus core 71.

9-2. Operation

Then, the operation of the ultrasonic probe and the ultrasonic diagnostic apparatus according to the ninth embodiment will be described. A refrigerant is fed to the refrigerant tube 77a with the feed pump 75a, and the refrigerant is supplied to the heat receiving part 73 in the probe unit 72 via the refrigerant tube 77a. The refrigerant arrived at the heat receiving part 73 through the refrigerant tube 77a absorbs the heat within the probe unit 72. Then, by the suction with the suction pump 75b, the refrigerant is sucked to the suction pump 75b from the heat receiving part 73 of the probe unit 72 via the refrigerant tube 77b. The refrigerant sucked to the suction pump 75b is fed to the radiator 76 by the suction pump 75b.

The refrigerant fed to the radiator 76 is passed within the header pipe 76a in arrow A direction shown in FIGS. 17 and 18. Furthermore, the refrigerant is fed to a number of the refrigerant channels 76c from the header pipe 76a of the radiator 76. During passing of the refrigerant through a number of the refrigerant channels 76c, the heat of the refrigerant is radiated outside the refrigerant channels 76c so that the refrigerant is cooled.

Due to the contact of the plate-like radiator 76 with the inside of the connector case 82, the heat radiated from surfaces of the refrigerant channels 76c is directly conducted to the connector case 82, and the heat conducted is radiated outside the connector case 82.

Then, the refrigerant is fed outside the radiator 76 (in arrow B direction) from the header pipe 76b through a number of the refrigerant channels 76c, and is passed to the suction pump 75b via the refrigerant tube 77d. In such a manner, by providing a number of the refrigerant channels 76c, the surface area (radiation area) of the radiator 76 is increased, so that the radiation efficiency is improved and the refrigerant can be sufficiently cooled by passing through the radiator 76.

The refrigerant cooled by the radiator 76 and fed to the feed pump 75a is again delivered to the heat receiving part 73 of the probe unit 72 by the feed pump 75a via the refrigerant tube 77a. In such a manner, the heat received in the heat receiving part 73 is radiated with the radiator 76, and the cooled refrigerant is circulated with the pumps 75a and 75b, suppressing the heat accumulation within the probe unit 72.

9-3. Effect

As described above, by arranging a number of the refrigerant channels 76c to increase the surface area of the radiator 76, a rate of the surface area (radiation area) of the radiator 76 can be increased compared to the size of it. In other words, even if the radiator 76 is to be smaller in size, the surface area (radiation area) can be increased, thereby improving radiation efficient at a small size. The smaller radiator 76 makes it possible to reduce the connector case 82 housing the radiator 76 in size, thereby reducing the ultrasonic probe in size.

Furthermore, since a number of the refrigerant channels 76c arranged in parallel forms the radiator 76, the radiator 76 becomes plate-shaped as a whole. This plate-shaped radiator 76 is arranged along to an inside surface of the connector case 82. For example, the radiator 76 is contacted to an inside surface of the connector case 82. Therefore, the heat generated from the radiator 76 is directly conducted to the connector case 82 so that the heat is radiated to outside of the probe connector part 74, thereby improving heat radiation efficient. In addition, the plate-shaped radiator 76 is arranged along to inside surface of the connector case 82. Therefore, the space occupied by the radiator 76 can be reduced in the connector case 82, resulting in the miniaturizing of the ultrasonic probe with improving heat radiation efficient of the radiator 76.

Figure 19:
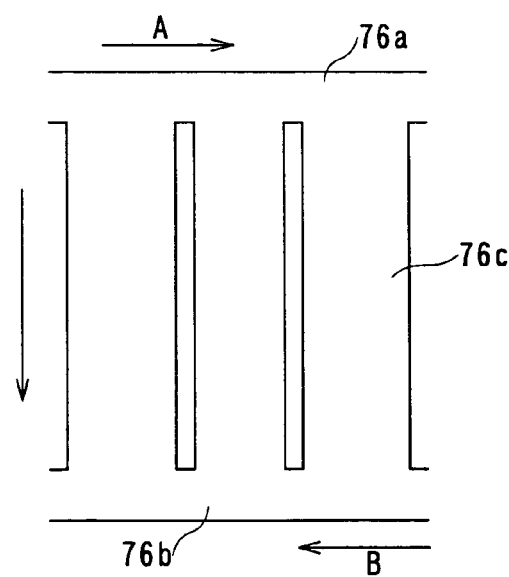
FIG. 19 is a structural drawing showing a modified example of the endotherm unit shown in FIG. 18.

In addition, the present invention is not limited to the radiator 76 shown in FIGS. 17 and 18, so that even when the radiator 76 shown in FIG. 19 is used, for example, the operation and the advantages of the present invention can be obtained. FIG. 19 is a structural drawing showing a modified example of the radiator 76 shown in FIG. 18.

In the radiator 76 shown in FIG. 18, the width of the individual refrigerant passage 76c is narrow and a number of the refrigerant channels 76c are connected together. In the radiator 76 shown in FIG. 19, three refrigerant channels 76c are connected together in parallel with each other, so that the width of the individual refrigerant passage 76c becomes wide. In such a manner, even when the number of the refrigerant channels 76c is reduced so as to increase the width of the individual refrigerant passage 76c, the operation and the advantages of the present invention can also be obtained.

In the radiator 76 according to the ninth embodiment, a plurality of the refrigerant channels 76c are connected together in parallel with each other; however, the present invention is not limited to this. For example, by folding one refrigerant passage at a plurality of times, the whole structure may be plate-shaped. According to the embodiment, one radiator 76 is provided; alternatively, on any internal surfaces of the connector case 82, the radiators 76 may be provided.

10. Tenth Embodiment

Figure 20:
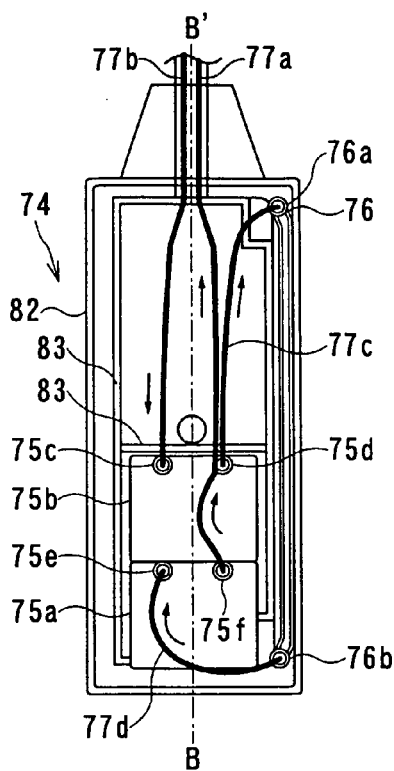
FIG. 20 is a front view of a probe connector part of an ultrasonic probe according to a tenth embodiment of the present invention.
Figure 21:
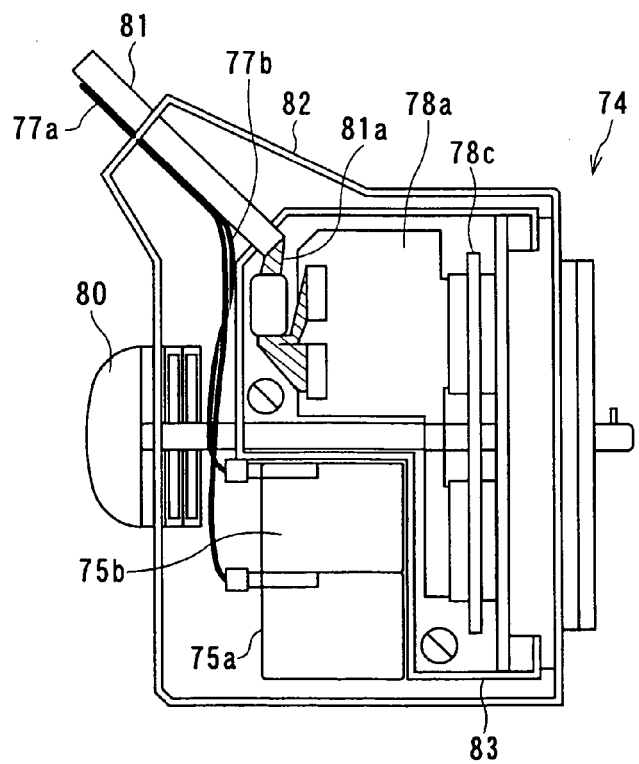
FIG. 21 is a sectional view of the probe connector part along the line segment B-B' shown in FIG. 20.

A summary structure of a probe connector part according to the tenth embodiment of the present invention will be described with reference to FIGS. 20 and 21. FIG. 20 is a front view of a probe connector part of an ultrasonic probe according to the tenth embodiment of the present invention. FIG. 21 is a sectional view of the probe connector part along the line segment B-B' shown in FIG. 20.

A probe connector part according to the tenth embodiment is substantially the same in configuration as the probe connector part according to the ninth embodiment; however, the point differs in that electric components built in the connector case 82, such as the circuit board 78a, are spaced from the cooling unit including the radiator 76 with a heat insulating partition member 83 therebetween.

Specifically, electrical components, such as the signal lines 81a and the circuit board 78a, are spaced from the radiator 76, the pumps 75a and 75b, and the refrigerant tube 77a with the heat insulating partition member 83 therebetween. The partition member 83 is arranged within the connector case 82 so as to surround the electrical components including the signal lines 81a and the circuit board 78a, and the radiator 76, the pumps 75a and 75b, and the refrigerant tube 77a are arranged outside the partition member 83. That is, the electric system is divided from the cooling system. The partition member 83 is made of a low heat-conductive material including a non-metallic material. For example, the partition member 83 is made of a resin such as a plastic.

In the ultrasonic probe with large heat-generation to an extent needing a cooling unit, it is assumed that there is a heat source, such as the circuit board 78a, also inside the probe connector part 74. Therefore, the heat generated by the electric system, such as the circuit board 78a, may reduce the radiation efficiency of the radiator 76.

In an ultrasonic probe connector 4 according to the tenth embodiment, the cooling unit including the radiator 76 and the pumps 75a and 75b is spaced from the heat source, such as the circuit board 78a, with the heat insulating partition member 83 therebetween, so that the heat generated from the heat source including the circuit board 78a is difficult to be conducted to the cooling unit including the radiator 76 and the pumps 75a and 75b, thereby preventing the reduction in radiation efficiency of the radiator 76.

In the cooling unit including the radiator 76, the pumps 75a and 75b, and the refrigerant tube 77a, the refrigerant circulates. The leakage of the circulating refrigerant through the radiator 76 or the refrigerant tube 77a may cause short-circuit of the electric components such as the circuit board 78a and the signal lines 81a. In the probe connector part 74 according to the tenth embodiment, the electric system, such as the circuit board 78a, is housed within the partition member 83 and spaced from the cooling unit including the radiator 76 and the pumps 75a and 75b, so that even the refrigerant leaks from the cooling system including the radiator 76, the refrigerant cannot be in contact with the electric system, such as the circuit board 78a. Therefore, electric components cannot be short-circuited.

11. Eleventh Embodiment 11-1. Constitution

Figure 22:
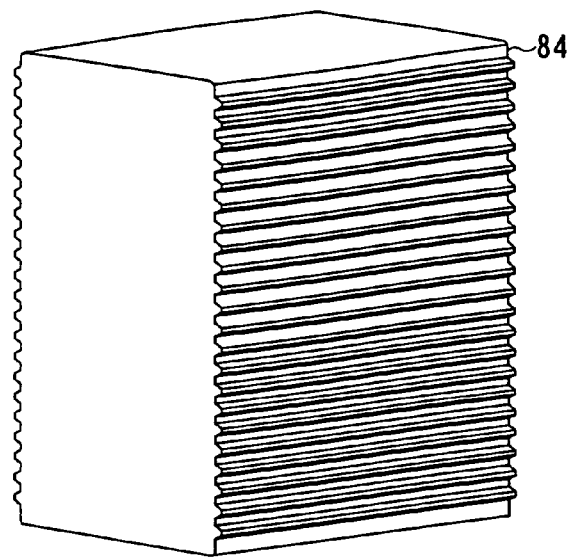
FIG. 22 is a perspective view of a connector case included in a probe connector part of an ultrasonic probe according to an eleventh embodiment of the present invention.
Figure 23:
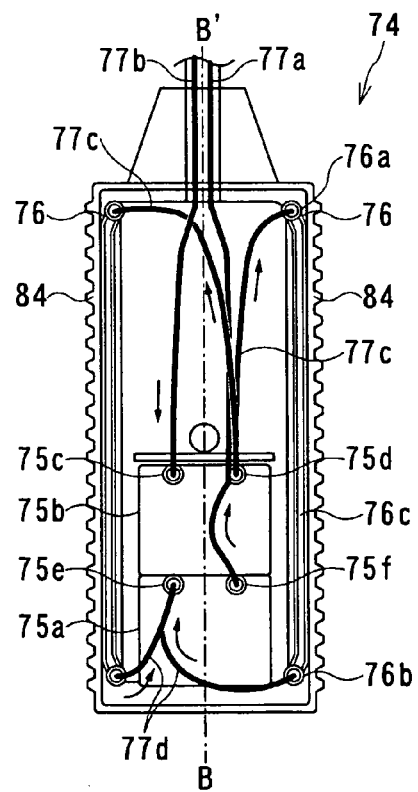
FIG. 23 is a front view of the probe connector part shown in FIG. 22.

A summary structure of a probe connector part according to the eleventh embodiment of the present invention will be described with reference to FIGS. 22 and 23. FIG. 22 is a perspective view of a connector case included in a probe connector part of an ultrasonic probe according to the eleventh embodiment of the present invention. FIG. 23 is a front view of the probe connector part shown in FIG. 22.

A probe connector part according to the eleventh embodiment is substantially the same in configuration as the probe connector part according to the ninth embodiment; however, the shape of the connector case differs therefrom. FIG. 22 shows only a connector case 84 of the probe connector part 74. In practice, from the connector case 84, the cable 81 having the signal lines 81a and the refrigerant tubes 77a and 77b built therein extends to the probe unit 72.

As shown in FIGS. 22 and 23, both lateral faces of the connector case 84 are roughened so as to have uneven surfaces. This increases the radiation area larger than that when the both lateral faces are flat, so that the lateral faces function as cooling fins. It is preferable for the material of the connector case 84 to be heat-conductive and heat-radiative highly like aluminum (Al); however, the present invention is not limited to these materials so that metals such as copper (Cu) and alloys such as SUS may also be used.

The bonding method between the radiator 76 and the connector case 84 preferably includes firm one such as welding and brazing in view of thermal conduction; alternatively, it may include screwing using heat-conductive silicone grease therebetween so as to secure sufficient heat conductivity.

Since the radiator 76 is installed on the internal surface of the connector case 84 in contact therewith in the same way as in the embodiments described above, the heat of the refrigerant passing through the radiator 76 is transmitted to the internal surface (lateral surfaces) of the connector case 84 and radiated outside therefrom. Because of the uneven lateral surfaces, the radiation area is increased larger than that of the flat lateral surfaces so as to radiate more heat quantity. As the heat-radiation is improved in such a manner, the heat of the refrigerant passing through the radiator 76 can be efficiently radiated outside the connector case 84, resulting in improvement in cooling capacity of the cooling system.

Furthermore, according to the eleventh embodiment, as shown in FIG. 23, the radiators 76 are installed on both lateral faces of the connector case 84. This allows the heat of the refrigerant passing through the radiators 76 to be radiated outside from both surfaces of the connector case 84, so that the heat radiation is further improved, resulting in further improvement in cooling capacity of the cooling system.

11-2. Operation

Then, the operation of the ultrasonic probe and the ultrasonic diagnostic apparatus according to the eleventh embodiment will be simply described. A refrigerant is fed to the refrigerant tube 77a with the feed pump 75a, and the refrigerant is supplied to the heat receiving part 73 in the probe unit 72 via the refrigerant tube 77a. The refrigerant arrived at the heat receiving part 73 through the refrigerant tube 77a absorbs the heat within the ultrasonic probe. Then, by the suction with the suction pump 75b, the refrigerant is sucked to the suction pump 75b from the heat receiving part 73 of the probe unit 72 via the refrigerant tube 77b. The refrigerant sucked to the suction pump 75b is fed to the two radiators 76 arranged in the both side of the connector case 84 via the refrigerant tube 77c.

The refrigerant fed to the radiators 76 is passed to a number of the refrigerant channels 76c via the header pipes 76a. During passing of the refrigerant through a number of the refrigerant channels 76c, the heat of the refrigerant is radiated outside the radiators 76 so that the refrigerant is cooled. Since lateral faces of the connector case 84 have an uneven shape so as to form cooling fins, the radiation area is increased so as to efficiently dissipate the heat of the refrigerant outside the connector case 84. Then, the refrigerant is fed outside the radiators 76 from the header pipe 76b through a number of the refrigerant channels 76c, and is passed to the feed pump 75a from the two radiators 76 via the refrigerant tube 77d.

In such a manner, by connecting a number of the refrigerant channels 76c together in parallel with each other as well as by roughening lateral faces of the connector case 84 so as to form fins, the radiation areas of the radiators 76 and the connector case 84 are increased, so that the radiation efficiency is further improved. Since the size of the radiator 76 need not be increased for improving the radiation efficiency, the ultrasonic probe can be miniaturized.

Furthermore, the near surface in which the radiator 76 was installed, among surfaces of the outer side of the connector case 84, is made uneven. Therefore, the heat radiated heat from the radiator 76 snd transmitted to the connector case 84 is easy to be radiated outside from the connector case 84, thereby improving the efficiency of radiation.

The refrigerant cooled by the two radiators 76 and fed to the feed pump 75a is again delivered to the heat receiving part 73 of the probe unit 72 by the feed pump 75a via the refrigerant tube 77a.

In addition, according to the eleventh embodiment, the radiators 76 are installed on both lateral faces of the connector case 84; alternatively, the radiator 76 may be arranged only on one side like in the probe connector parts according to the ninth and tenth embodiments. When the radiator 76 is arranged only on one side, the external lateral face adjacent to the radiator 76 is roughened. In such a manner, by roughening the external lateral face of the connector case 84 in accordance with the installation site of the radiator 76, the heat radiated from the radiator 76 and transmitted to the connector case 84 is liable to be radiated outside, improving the radiation efficiency.

In the probe connector part according to the ninth and tenth embodiments, by installing the radiators 76 on both lateral faces of the connector case, the cooling capacity of the cooling system may also be increased by improving the radiation of the radiator 76.

12. Twelfth Embodiment

Figure 24:
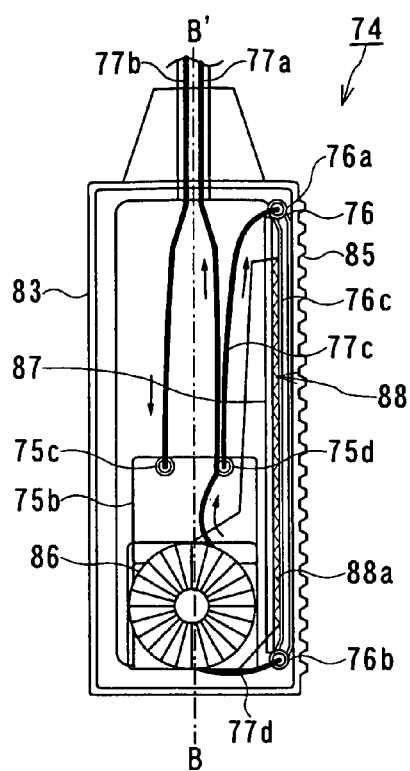
FIG. 24 is a front view of a probe connector part of an ultrasonic probe according to a twelfth embodiment of the present invention.
Figure 25:
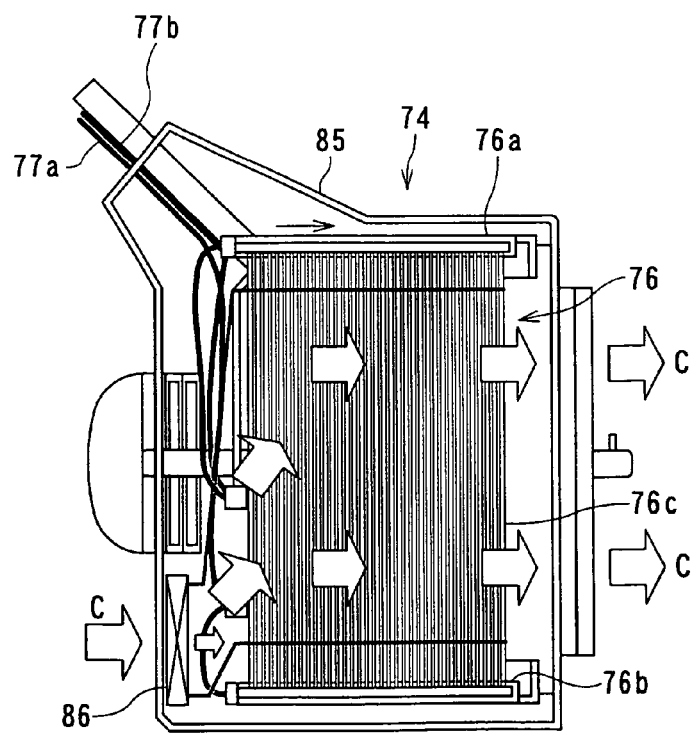
FIG. 25 is a sectional view of the probe connector part along the line segment B-B' shown in FIG. 24.

A summary structure of a probe connector part according to the twelfth embodiment of the present invention will be described with reference to FIGS. 24 and 25. FIG. 24 is a front view of a probe connector part of an ultrasonic probe according to the twelfth embodiment of the present invention. FIG. 25 is a sectional view of the probe connector part along the line segment B-B' shown in FIG. 24.

A probe connector part according to the twelfth embodiment also includes the pumps 75a and 75b and the radiator 76 arranged on one side of the connector case 85 in the same way as in the probe connector part according to the ninth embodiment; furthermore, it includes a cooling fan 86 within the connector case 85. The cooling fan 86 is arranged in the connector case 85 on its front surface side, for example, so as to take ambient air into the connector case 85 from the outside of the connector case 85.

In the same way as in the probe connector part according to the tenth embodiment, the electric components, such as the circuit board 78a, are housed within the partition member 83 and spaced from the cooling system including the radiator 76 and the pumps 75a and 75b.

Furthermore, a heat insulating material 87 is provided between the radiator 76 and the partition member 83. Between the radiator 76 and the heat insulating material 87, a minute gap is formed to extend in the juxtaposing direction of the refrigerant channels 76c. The minute gap forms an air channel 88, and the ambient air taken in by the cooling fan 86 from the front surface of the connector case 85 flows through the air channel 88 so as to pass through toward the rear surface (surface remote from the cooling fan 86) of the connector case 85 (arrow C direction).

The ambient air may also be taken in from the rear surface of the connector case 85 so as to pass through toward the front surface of the connector case 85 (opposite to arrow C direction). More specifically, the cooling fan 86 may not be used for suction, but for discharge. When the cooling fan 86 is used for discharge so as to form a flow of the ambient air in the opposite to arrow C direction, it is expectable to form the flow of the flatter ambient air.

The air channel 88 is provided with a radiation plate 88a made of a metal, such as copper, and connected to the radiator 76 and the heat insulating material 87. The radiation plate 88a is arranged between the radiator 76 and the heat insulating material 87 in a state folded at a plurality of times.

Also, in the connector case 85, the external surface adjacent to the radiator 76 is roughened so as to function as cooling fins. According to the twelfth embodiment, the radiator 76 is provided only on one side; alternatively, the radiators 76 may be provided on both sides like in the ultrasonic probe connector according to the eleventh embodiment. Moreover, external both side surfaces of the connector case 85 may be roughened.

According to the probe connector part 74 constructed as described above, with the cooling fan 86 provided inside the connector case 85, ambient air is taken into from the outside of the connector case 85. The taken ambient air flows through the air channel 88 formed between the radiator 76 and the heat insulating material 87 so as to be discharged outside the connector case 85 from an outlet (not shown) formed on the rear side of the connector case 85, for example (the ambient air flows through in arrow C direction). The radiator 76 is brought into contact with the ambient air in such a manner, so that not only from the lateral surface of the connector case 85, but also with the ambient air, the heat from the radiator 76 is discharged to the outside, thereby efficiently reducing the temperature of the refrigerant passing through the radiator 76.

When the heat value is increased in the probe unit 72 so that the more improved heat radiation efficiency is demanded, it is necessary to improve the cooling efficiency by the refrigerant in the radiator 76. According to the twelfth embodiment, the cooling fan 86 is provided within the connector case 85 so as to forcedly cool the radiator 76, so that the temperature of the refrigerant flowing through the radiator 76 can be further reduced efficiently.

13. Thirteenth Embodiment

Figure 26:
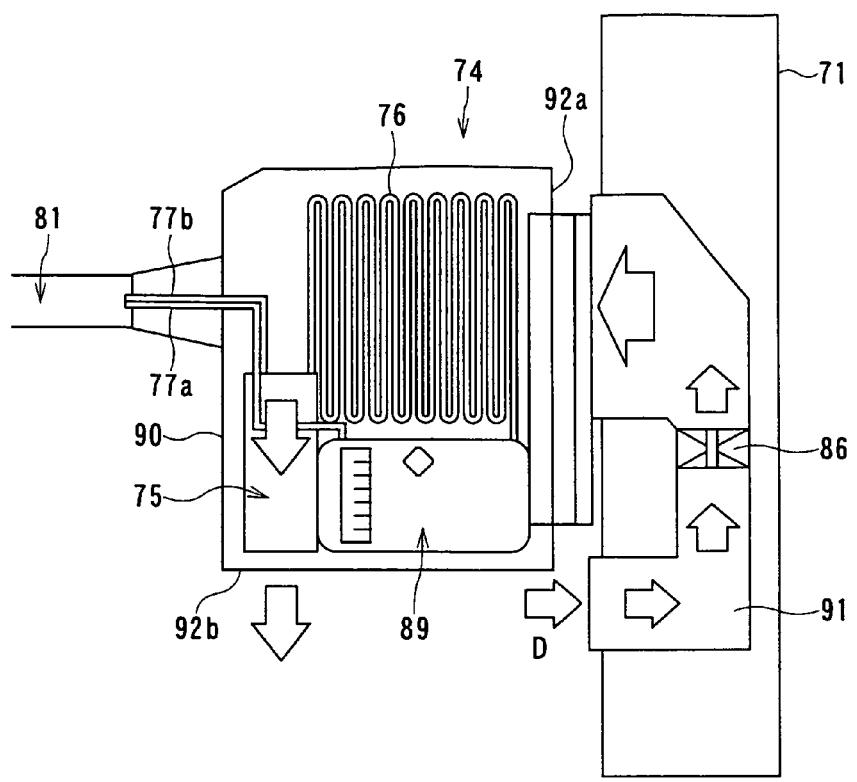
FIG. 26 is a side view of a probe connector part of an ultrasonic probe and an ultrasonic diagnostic apparatus core according to a thirteenth embodiment of the present invention.
Figure 27:
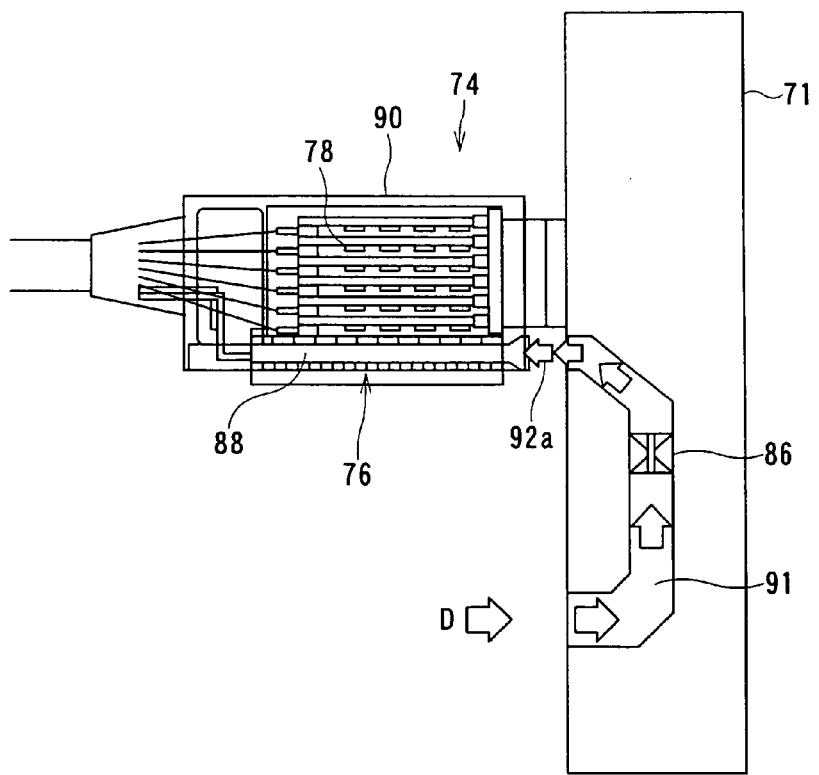
FIG. 27 is a top view of the probe connector part and the ultrasonic diagnostic apparatus core shown in FIG. 26.

A probe connector part and an ultrasonic diagnostic apparatus core according to the thirteenth embodiment of the present invention will be described with reference to FIGS. 26 and 27. FIG. 26 is a side view of a probe connector part of an ultrasonic probe and an ultrasonic diagnostic apparatus core according to the thirteenth embodiment of the present invention. FIG. 27 is a top view of the probe connector part and the ultrasonic diagnostic apparatus core shown in FIG. 26.

A probe connector part according to the thirteenth embodiment includes the pump 75 in the same way as in the probe connector part according to the ninth embodiment, and it also includes the radiator 76 on one side of a connector case 90. According to the thirteenth embodiment, with the one pump 75 provided, the refrigerant is fed and sucked. By folding a refrigerant tube made of a metal, such as copper, the radiator 76 has a plate-like shape as a whole. Furthermore, a refrigerant tank 89 is provided within the connector case 85 for temporarily storing the refrigerant.

Furthermore, in the same way as in the probe connector part according to the twelfth embodiment, within the connector case 90, a heat insulating material (not shown) is provided along the radiator 76, and the air channel 88 is formed between the heat insulating material and the radiator 76. Different from the twelfth embodiment, the cooling fan 86 is not arranged within the connector case 90 but within an ultrasonic diagnostic apparatus core 71. Inside the ultrasonic diagnostic apparatus core 71, an air channel 91 is provided for passing ambient air into the connector case 90. The cooling fan 86 is arranged inside the air channel 91 so as to take ambient air into the ultrasonic diagnostic apparatus core 71 from the outside of the ultrasonic diagnostic apparatus core 71 (arrow D direction). The taken ambient air is fed into the probe connector part 74.

Note that, the cooling fan 86 may not be used for suction, but for discharge like the twelfth embodiment. When a flow of the ambient air is formed in the opposite to arrow D direction, it is expectable to form the flow of the flatter ambient air.

In the connector case 90 of the probe connector part 74, an opening 92a is formed adjacent to the ultrasonic diagnostic apparatus core 71 for introducing the ambient air fed from the ultrasonic diagnostic apparatus core 71 into the connector case 90. From the opening 92a, the ambient air is taken into the connector case 90 so as to be exhausted to outside thereof from an outlet 92b formed on the front bottom of the connector case 90 via the air channel 88.

The radiator 76 is brought into contact with ambient air, so that not only from the lateral surface of the connector case 90, but also with the ambient air, the heat from the radiator 76 is discharged to the outside, thereby efficiently reducing the temperature of the refrigerant passing through the radiator 76. Moreover, by providing the cooling fan 86 in the ultrasonic diagnostic apparatus core 71, the probe connector part 74 can be miniaturize by the size of the cooling fan 86.

Then, the operation of the ultrasonic diagnostic apparatus according to the thirteenth embodiment will be simply described. With the pump 75, a refrigerant is sucked from the refrigerant tank 89 so as to feed it to the heat receiving part 73 of the probe unit 72 via the refrigerant tube 77a. Then, in the same way as in the embodiments described above, the heat generated in the probe unit 72 is absorbed in refrigerant in the heat receiving part 73. The refrigerant returns to the probe connector part 74 by being sucked to the pump 75 via the refrigerant tube 77b. Then, the refrigerant with a temperature increased by absorbing the heat of the probe unit 72 is supplied to the radiator 76 with the pump 75. Since the radiator 76 is closely attached on the internal surface of the connector case 90, the heat of the refrigerant is radiated outside the connector case 90 via the lateral surface of the connector case 90 with the radiator 76. Furthermore, with the ambient air fed by the cooling fan 86, the temperature of the radiator 76 is reduced, thereby decreasing the temperature of the refrigerant. The refrigerant with a temperature decreased by the radiator 76 is fed to the refrigerant tank 89 from the radiator 76 by the pump 75 so as to be stored therein. Then, with the pump 75, the refrigerant is again fed to the heat receiving part 73 of the probe unit 72 from the refrigerant tank 89. By repeating this series of processes, the temperature increase of the probe unit 72 is suppressed.

14. Fourteenth Embodiment 14-1. Constitution

Figure 28:
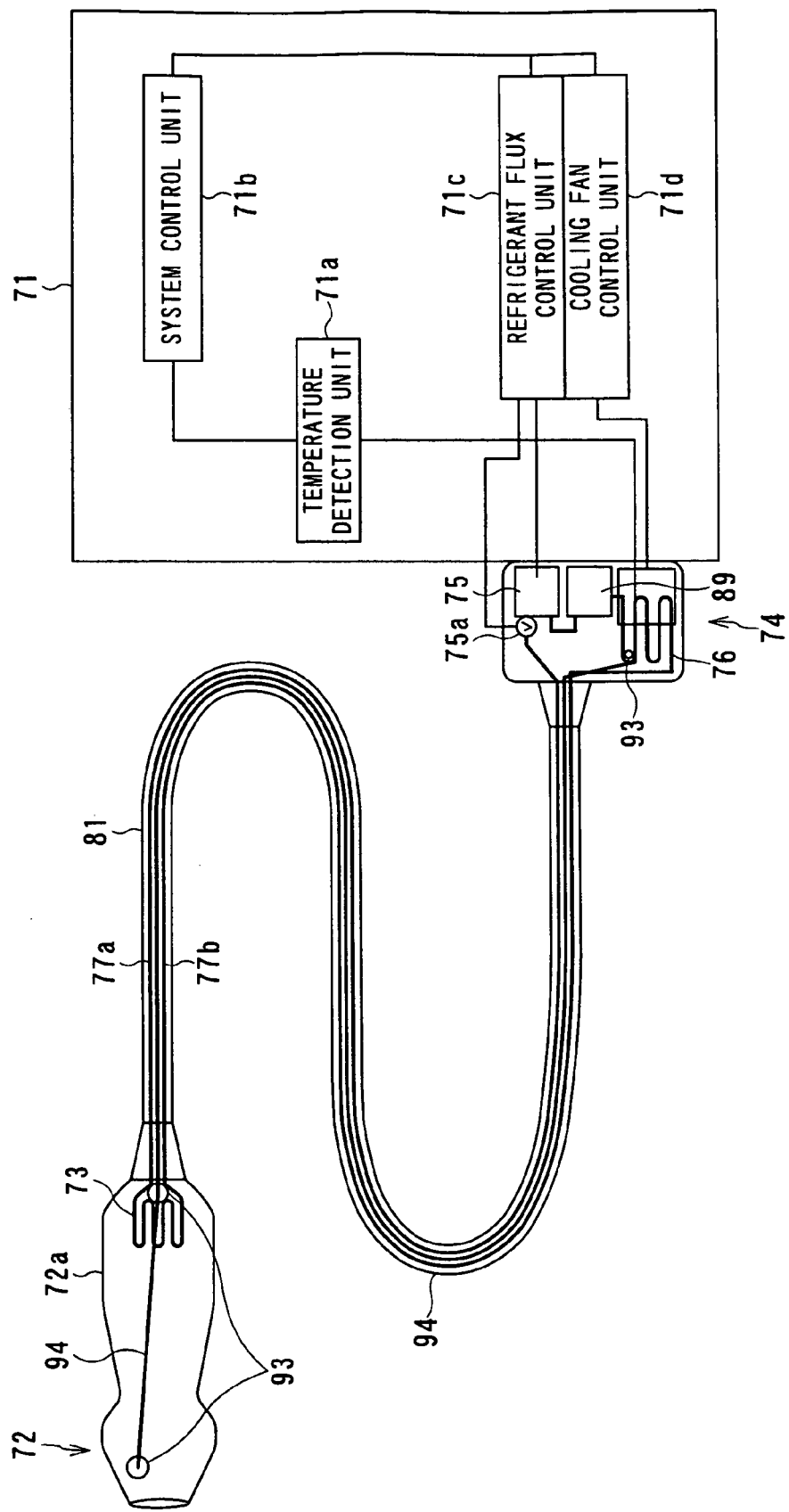
FIG. 28 is a diagram showing a summary structure of an ultrasonic probe and an ultrasonic diagnostic apparatus core according to a fourteenth embodiment of the present invention.
Figure 29:
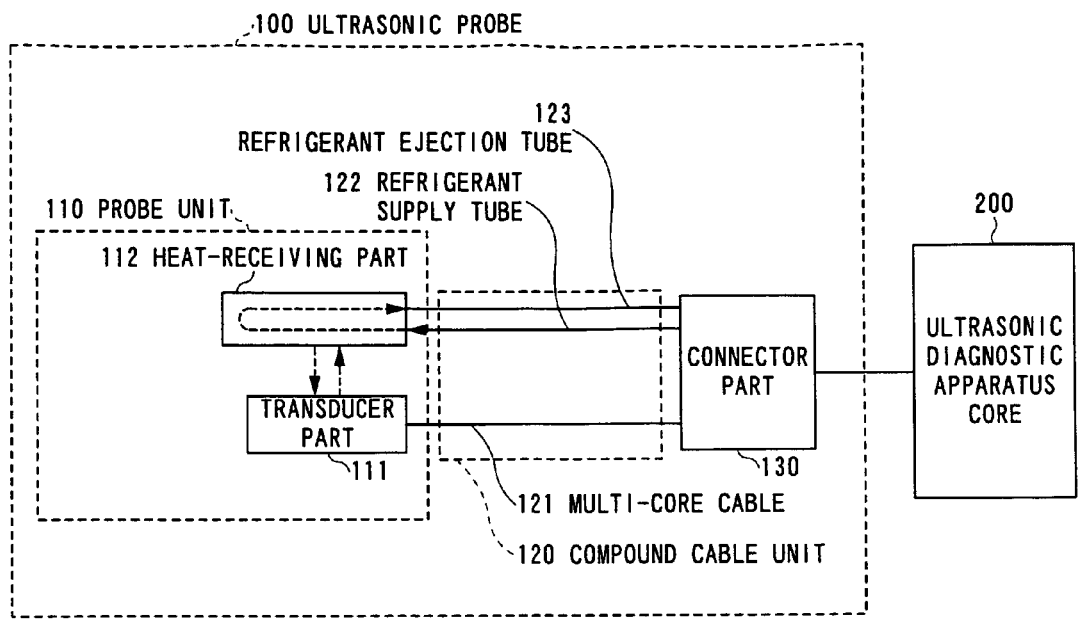
FIG. 29 is a diagram showing an example of a structure of a conventional ultrasonic probe having a cooling mechanism.
Figure 30:
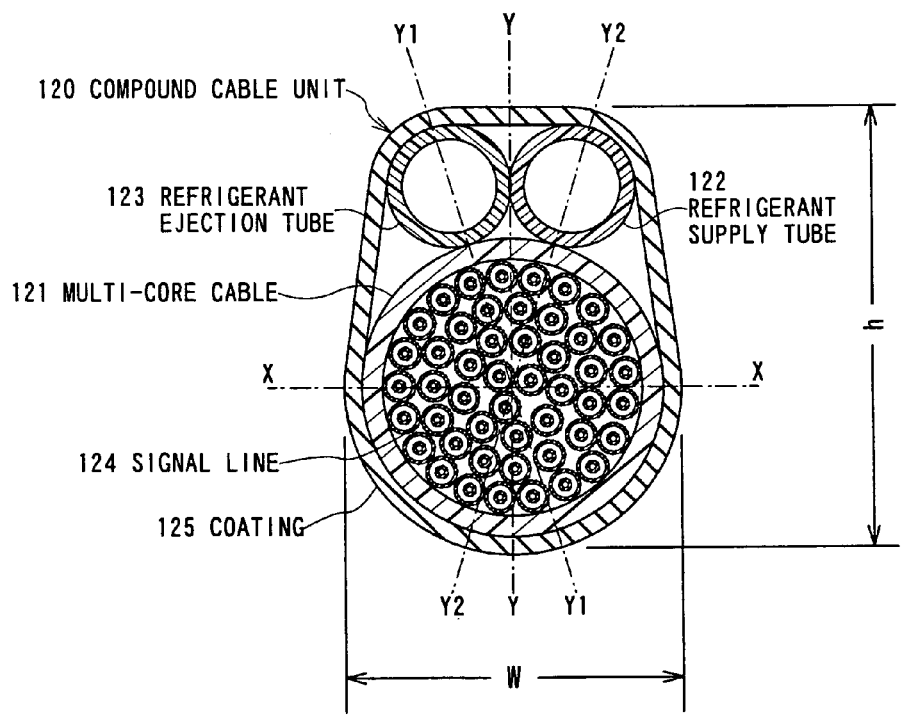
FIG. 30 is a diagram showing a section of the conventional compound cable unit shown in FIG. 29.

An ultrasonic diagnostic apparatus according to the fourteenth embodiment of the present invention will be described with reference to FIG. 28. FIG. 28 is a diagram showing a summary structure of an ultrasonic probe and an ultrasonic diagnostic apparatus core according to the fourteenth embodiment of the present invention.

In an ultrasonic probe according to the fourteenth embodiment, at least one of the temperature of the probe unit 72 and the temperature of a refrigerant is detected, and the probe unit 72 is maintained in a safety temperature range by controlling the operation of the pump 75 or the cooling fan 86 of the cooling unit on the basis of the detected result.

If the cooling unit including the pump 75 and the radiator 76 is always operated with its full power, the temperature rise of the probe unit 72 can be suppressed to a minimum. However, if the cooling capacity of the cooling unit is designed to be large in accordance with the assumed high heat value of the probe unit 72, under the operating conditions of the probe unit 72, such as the condition that the probe unit 72 is scarcely heated, or the small rise in temperature of the probe unit 72 due to a low ambient temperature, when the probe unit 72 is cooled with the designed cooling power, the temperature in the ultrasonic probe is reduced to excess, so that dew condensation may be generated in the probe unit 72. Since the cooling unit includes electric components such as the pump 75 and the cooling fan 86, electric power is consumed by the operation of the cooling unit. At the temperature not necessary for the cooling, if the cooling unit is always operated with its full power, electric power is consumed in vain.

Then, in the ultrasonic diagnostic apparatus according to the fourteenth embodiment, the temperature of the probe unit 72 or the temperature of the refrigerant is detected, and the generation of dew condensation and useless electric power consumption due to the excess cooling are suppressed by controlling the operation of the cooling unit on the basis of the detected result.

The structures of the probe unit 72 and the probe connector part 74 provided in the ultrasonic diagnostic apparatus according to the fourteenth embodiment are substantially the same as those according to the ninth to thirteenth embodiments. In FIG. 28, the probe connector part according to the thirteenth embodiment is shown as a representative; alternatively, it may be one of the probe connector parts according to the ninth to twelfth embodiments.

According to the fourteenth embodiment, a temperature detection unit (temperature sensor) 93 is provided within the probe unit 72 or the probe connector part 74. When the temperature detection unit 93 is arranged within the probe unit 72, the temperature detection unit 93 is arranged at least at any one of the position adjacent to the piezoelectric transducers as the heating source (close to the surface of the probe unit 72), the position in the vicinity of the heat receiving part 73, and the position in the vicinity of the circuit board (not shown). Hence, for monitoring temperatures of a plurality of positions, the temperature detection units 93 may be arranged at a plurality of positions, or for monitoring the temperature of one position, the temperature detection unit 93 may be arranged only at one position. By arranging the temperature detection unit 93 within the probe unit 72 in such a manner, the temperature of the probe unit 72 is monitored.

When the temperature detection unit 93 is arranged within the probe connector part 74, the temperature detection unit 93 is arranged at least at the position in the vicinity of the radiator 76 or the position in the vicinity of the refrigerant tank 89. In this case, the temperature detection units 93 may also be arranged at a plurality of positions, or the temperature detection unit 93 may be arranged only at one position. By arranging the temperature detection unit 93 at the position in the vicinity of the radiator 76 or the refrigerant tank 89 in such a manner, the temperature of the refrigerant is monitored. Alternatively, the temperature detection units 93 may be arranged in both the probe unit 72 and the probe connector part 74 so that both the temperatures are monitored.

When monitoring the surface temperature of the probe unit 72 directly, the temperature detection unit 93 may be arranged at a position in the probe unit 72 close to its surface (the position adjacent to the piezoelectric transducers). Even if the temperature detection unit 93 is not arranged at a position in the probe unit 72 close to its surface in such a manner, when the peripheral temperature is detected by arranging the temperature detection unit 93 in the vicinity of the circuit board (not shown) in the probe unit 72 or in the vicinity of the heat receiving part 73, the surface temperature can also be monitored indirectly. Also, the temperature in the probe unit 72 can also be indirectly monitored by assuming the heat value absorbed in the heat receiving part 73 by arranging the temperature detection unit 93 in the vicinity of the radiator 76 within the connector case so as to monitor the temperature of the refrigerant.

A signal line 94 is connected to the temperature detection unit 93 so that an electric signal indicating a temperature detected by the temperature detection unit 93 is outputted to an ultrasonic diagnostic apparatus core 71 via the signal line 94.

The ultrasonic diagnostic apparatus core 71 has a temperature detection unit 71a, a system control unit 71b, a refrigerant flux control unit 71c and a cooling fan control unit 71d for controlling a cooling system.

The temperature detection unit 71a calculates the temperature on the basis of the electric signal from the temperature detection unit 93. The system control unit 71b obtains the drive condition of the cooling unit, in which the surface temperature of the probe unit 72 is included in a safety temperature range, from the drive state of the probe unit 72 and the temperature calculated by the temperature detection unit 71a so as to output a control signal to the refrigerant flux control unit 71c or the cooling fan control unit 71d. The safety temperature range herein means a temperature range being safe even when the probe unit 72 is brought into contact with the object. In general, the safety temperature range is from 30° C. to 50° C., so that the drive condition of the cooling unit, in which the surface temperature of the probe unit 72 is included in this temperature range, is obtained.

For example, a coordinate table between the temperature detected by the temperature detection unit 93 and the drive condition of the cooling unit for maintaining the surface temperature of the probe unit 72 within the safety temperature range is prepared in advance so as to store the table in a memory (not shown) provided in the ultrasonic diagnostic apparatus core 71.

Specifically, a coordinate table between the temperature detected by the temperature detection unit 93 and the flow rate of the refrigerant, a coordinate table between the detected temperature and the drive voltage to be applied to the pump 75, and a coordinate table between the detected temperature and the drive voltage to be applied to the cooling fan 86 are prepared and stored in the memory in advance. Then, the system control unit 71b refers to the tables stored in the memory on the basis of the detected temperature so as to obtain the flow rate of the refrigerant for maintaining the surface temperature of the probe unit 72 within the safety temperature range and the drive voltage of the pump 75 or the cooling fan 86. The control signals indicating the obtained drive voltage and so forth are outputted to the refrigerant flux control unit 71c or the cooling fan control unit 71d.

The refrigerant flux control unit 71c is connected to the pump 75 so as to change the drive voltage to be applied to the pump 75 and the valve travel of the flow regulating valve 76a for adjusting the flow rate on the basis of the control signal outputted from the system control unit 71b. The cooling fan control unit 71d is connected to the cooling fan 86 so as to change the voltage or the frequency of driving signal to be applied to the cooling fan 86 on the basis of the control signal outputted from the system control unit 71b.

14-2. Operation

The operation of the ultrasonic diagnostic apparatus constructed as described above will be described. First, with the temperature detection unit 93 arranged within the probe unit 72 or the probe connector part 74, the surface temperature of the probe unit 72 and the peripheral temperature of the radiator 76 are detected. The case where the temperature detection unit 93 is arranged in the probe unit 72 close to its surface (adjacent to ultrasonic transducers) will be described herein.

The electric signal corresponding to the surface temperature of the probe unit 72 detected by the temperature detection unit 93 is outputted to the temperature detection unit 71a provided in the ultrasonic diagnostic apparatus core 71 through signal lines 94. The temperature detection unit 71a calculates the surface temperature of the probe unit 72 using the received electric signal so as to output the temperature information to the system control unit 71b. The system control unit 71b obtains the drive condition of the cooling system for maintaining the surface temperature of the probe unit 72 within the safety temperature range on the basis of the temperature information.

If the detected temperature is high, the cooling power of the cooling system is increased while if the detected temperature is low, the cooling power of the cooling system is reduced. That is, with increasing temperature detected, the cooling power of the cooling system is increased. For example, the cooling power is controlled by changing the drive condition of the pump 75 so as to adjust the flow rate of the refrigerant. If the detected temperature is high, the volume of the refrigerant fed to the heat receiving part 73 from the pump 75 is increased while if the detected temperature is low, the volume of the refrigerant fed to the heat receiving part 73 from the pump 75 is decreased.

In order to perform such control, the system control unit 71b refers to the tables stored in the memory (not shown) in the ultrasonic diagnostic apparatus core 71 so as to obtain the flow rate of the refrigerant from the tables and the detected temperature. In this case, a coordinate table between the detected temperature and the flow rate of the refrigerant for maintaining the temperature within the safety temperature range is prepared in advance and the flow rate of the refrigerant is obtained by referring to this table. Then, the drive voltage for passing the refrigerant at this flow rate is obtained so as to output this voltage information to the refrigerant flux control unit 71c.

Also, a coordinate table between the detected temperature and the drive voltage to be applied to the pump 75 for maintaining the temperature within the safety temperature range may be prepared in advance and the drive voltage may be obtained by referring to this table so as to output this voltage information to the refrigerant flux control unit 71c.

If the detected temperature is high, the drive voltage to be applied to the pump 75 is increased so as to increase the flow rate of the refrigerant supplied from the pump 75. On the other hand, if the detected temperature is low, the drive voltage to be applied to the pump 75 is reduced so as to decrease the flow rate of the refrigerant supplied from the pump 75. That is, with increasing temperature detected, the drive voltage to be applied to the pump 75 is increased so as to increase the flow rate of the refrigerant supplied from the pump 75.

The refrigerant flux control unit 71c drives the pump 75 at the drive voltage obtained from the system control unit 71b. With increasing temperature detected, the higher drive voltage is applied to the pump 75 so as to increase the flow rate of the refrigerant supplied from the pump 75. By changing the drive voltage to be applied to the pump 75 corresponding to the detected temperature in such a manner, the surface temperature of the probe unit 72 can be maintained within the safety temperature range. Moreover, since the probe unit 72 is not cooled to excess, the electric power cannot be consumed in vain. The generation of dew condensation due to excessive cooling can also be suppressed.

Not only by changing the drive voltage to be applied to the pump 75, but also by adjusting the aperture size (valve travel) of the flow regulating valve 76a provided in the pump 75 for regulating the flow rate of the refrigerant, the flow rate of the refrigerant fed to the heat receiving part 73 of the probe unit 72 from the pump 75 may also be regulated.

In order to perform such control, the system control unit 71b refers to the tables stored in the memory (not shown) in the ultrasonic diagnostic apparatus core 71 so as to obtain the flow rate of the refrigerant from the tables and the detected temperature. In this case, a coordinate table between the detected temperature and the flow rate of the refrigerant for maintaining the temperature within the safety temperature range is prepared in advance and the flow rate of the refrigerant is obtained by referring to this table. Then, the aperture size (valve travel) of the flow regulating valve 76a for passing the refrigerant at this flow rate is obtained so as to output this opening information to the refrigerant flux control unit 71c. Then, the aperture size of the flow regulating valve 76a is adjusted by the control of the refrigerant flux control unit 71c so as to regulate the flow rate of the refrigerant to be fed to the heat receiving part 73.

If the detected temperature is high, the aperture size of the flow regulating valve 76a is increased by the control of the refrigerant flux control unit 71c so as to increase the flow rate of the refrigerant supplied to the heat receiving part 73. On the other hand, if the detected temperature is low, the aperture size of the flow regulating valve 76a is reduced by the control of the refrigerant flux control unit 71c so as to decrease the flow rate of the refrigerant supplied to the heat receiving part 73. That is, with increasing temperature detected, the aperture size of the flow regulating valve 76a is increased so as to increase the flow rate of the refrigerant supplied from the pump 75. By changing the aperture size of the flow regulating valve 76a provided in the pump 75 corresponding to the detected temperature in such a manner, the surface temperature of the probe unit 72 can be maintained within the safety temperature range. Moreover, the generation of dew condensation due to excessive cooling can be suppressed.

When controlling the cooling power by adjusting the flow rate of the air flowing through the probe connector part 74, the system control unit 71b obtains the drive condition of the cooling fan 86. If the detected temperature is high, the rotational speed of the cooling fan 86 is increased so as to increase the flow rate of the ambient air taken into the probe connector part 74. The system control unit 71b obtains the drive voltage of the cooling fan 86 for increasing the flow rate of the ambient air to be taken so as to output the voltage information to the cooling fan control unit 71d. In this case, with increasing temperature detected, the drive voltage applied to the cooling fan 86 is also increased so as to increase the flow rate of the ambient air taken by the cooling fan 86.

In order to perform such control, the system control unit 71b refers to the tables stored in the memory (not shown) in the ultrasonic diagnostic apparatus core 71 so as to obtain the drive voltage of the cooling fan from the tables and the detected temperature. In this case, a coordinate table between the detected temperature and the drive voltage of the cooling fan for maintaining the temperature within the safety temperature range is prepared in advance, and the drive voltage of the cooling fan is obtained by referring to this table. Then, the voltage information is outputted to the cooling fan control unit 71d, and the rotational speed of the cooling fan 86 is adjusted by the control of the cooling fan control unit 71d so as to adjust the flow rate of the ambient air.

The cooling fan control unit 71d drives the cooling fan 86 at the drive voltage obtained from the system control unit 71b. With increasing temperature detected, the higher drive voltage is applied to the cooling fan 86 so as to increase the flow rate of the ambient air taken by the cooling fan 86. By changing the drive voltage to be applied to the cooling fan 86 corresponding to the detected temperature in such a manner, the surface temperature of the probe unit 72 can be maintained within the safety temperature range. Moreover, since the probe unit 72 is not cooled to excess, the electric power cannot be consumed in vain. The generation of dew condensation due to excessive cooling can also be suppressed.

With the changed frequency, the cooling fan 86 may be driven. With increasing temperature detected, the cooling fan control unit 71d drives the cooling fan 86 at a higher frequency so as to increase the rotational speed of the cooling fan 86 for increasing the flow rate of the ambient air to be taken. By controlling the frequency in such a manner, the operation and advantages of the present invention may also be obtained.

As described above, by changing the drive condition of the pump 75 or the cooling fan 86 on the basis of the detected temperature, the cooling can be performed in accordance with the temperature of the probe unit 72. As a result, the temperature of the probe unit 72 can be maintained within the safety temperature range, thereby suppressing the generation of dew condensation and the useless electric power consumption due to the excessive cooling.

In the examples described above, the surface temperature of the probe unit 72 is directly detected by arranging the temperature detection unit 93 in the probe unit 72 close to its surface; alternatively, by arranging the temperature detection unit 93 in the vicinity of the radiator 76 within the probe connector part 74, the temperature of the radiator 76 may be detected so as to indirectly monitor the temperature of the probe unit 72 for controlling it.

If the peripheral temperature of the radiator 76 is high, the heat value radiated from the radiator 76 is determined large. That is, in the heat receiving part 73, the heat absorbed by the refrigerant is determined large. In this case, the temperature of the probe unit 72 is determined high, so that when the detected temperature is high, the system control unit 71b and so forth increase the cooling power of the cooling system. As described above, by increasing the drive voltage to be applied to the pump 75 or by increasing the aperture size of the flow regulating valve 76a provided in the pump 75, the flow rate of the refrigerant to be fed to the probe unit 72 is increased. By increasing the drive voltage to be applied to the cooling fan 86, the flow rate of the ambient air taken from the outside is also increased.

On the other hand, if the peripheral temperature of the radiator 76 is low, the heat value radiated from the radiator 76 is determined small. That is, in the heat receiving part 73, the heat absorbed by the refrigerant is determined small. In this case, the temperature of the probe unit 72 is determined low, so that when the detected temperature is low, the system control unit 71b and so forth reduce the cooling power of the cooling system. As described above, by reducing the drive voltage to be applied to the pump 75 or by reducing the aperture size of the flow regulating valve 76a provided in the pump 75, the flow rate of the refrigerant to be fed to the probe unit 72 is decreased. By reducing the drive voltage to be applied to the cooling fan 86, the flow rate of the ambient air taken from the outside is also decreased.

In such a manner, by changing the drive voltage to be applied to the pump 75, the aperture size of the flow regulating valve 76a provided in the pump 75, or the drive voltage to be applied to the cooling fan 86 in accordance with the detected temperature (peripheral temperature of the radiator 76), the surface temperature of the probe unit 72 can be maintained within the safety temperature range. Also, since the probe unit 72 is not cooled to excess, the electric power cannot be consumed in vain. Furthermore, the generation of dew condensation due to excessive cooling can be suppressed.

In conclusion, the ultrasonic probe and the ultrasonic diagnostic apparatus constructed as mentioned above can adjust a cooling capacity so as to keep a necessary transmission sound energy flux with a safe surface temperature.

Various functions of the ultrasonic probe according to the first to the fourteenth embodiments described above may be combined so as to form an ultrasonic probe.

What is claimed is:

1. An ultrasonic probe comprising:
   a probe unit having a transducer part and a heat-receiving part, the transducer part being configured to transmit and receive an ultrasonic wave, the heat-receiving part being configured to absorb heat generated from the transducer part;
   a refrigeration unit configured to refrigerate the heat-receiving part; and
   a cable unit with a circular section having signal lines, a refrigerant supply tube, and a refrigerant ejection tube, the signal lines being configured to communicate signals between the transducer part and an ultrasonic diagnostic apparatus, the refrigerant supply tube being configured to supply a refrigerant from the refrigeration unit to the heat-receiving part, the refrigerant ejection tube being configured to send the refrigerant for ejecting heat of the heat-receiving part to the refrigeration unit;
   wherein a set of the refrigerant supply tube and the refrigerant ejection tube is arranged substantially at a center core of a cross-section of the cable unit, the signal lines being arranged to fill completely a 360° angular space circumferentially surrounding the set of the refrigerant supply tube and the refrigerant ejection tube, and the refrigerant supply tube and the refrigerant ejection tube are configured to be a common multi-channel tube with a circular section which has at least two independent channels in a length direction, at least one channel of the independent channels being used for the refrigerant supply tube while the other channel or the other channels of the independent channels are used for the refrigerant ejection tube.

2. The ultrasonic probe according to claim 1, wherein the multi-channel tube has a space on a partition between the refrigerant supply tube and the refrigerant ejection tube.

* * * * *